US009675768B2

(12) United States Patent
Fink et al.

(10) Patent No.: US 9,675,768 B2
(45) Date of Patent: *Jun. 13, 2017

(54) AEROSOLIZATION DEVICE

(71) Applicant: Nektar Therapeutics, San Francisco, CA (US)

(72) Inventors: James B. Fink, San Mateo, CA (US); Nani P. Kadrichu, San Carlos, CA (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/975,381

(22) Filed: Dec. 18, 2015

(65) Prior Publication Data

US 2016/0175545 A1    Jun. 23, 2016

Related U.S. Application Data

(63) Continuation of application No. 14/832,344, filed on Aug. 21, 2015, now Pat. No. 9,242,054, which is a
(Continued)

(51) Int. Cl.
*A61M 11/00*    (2006.01)
*A61M 15/00*    (2006.01)
(Continued)

(52) U.S. Cl.
CPC ........... *A61M 11/005* (2013.01); *A61M 11/02* (2013.01); *A61M 15/0015* (2014.02);
(Continued)

(58) Field of Classification Search
CPC ............... A61M 11/00; A61M 11/001; A61M 11/005–11/008; A61M 11/06–11/08; A61M 15/0085
See application file for complete search history.

(56) References Cited

U.S. PATENT DOCUMENTS 4,534,343 A    8/1985 Nowacki et al.
5,164,740 A    11/1992 Ivri
(Continued)

FOREIGN PATENT DOCUMENTS

DE    10 2005 006 374    7/2006
WO    WO 02/36181    5/2002
(Continued)

OTHER PUBLICATIONS

PCT International Search Report and Written Opinion corresponding to PCT Application No. PCT/US2009/002054 date of mailing Dec. 18, 2009.
(Continued)

*Primary Examiner* — Rachel Young
(74) *Attorney, Agent, or Firm* — Mark A. Wilson

(57) ABSTRACT

An aerosol transfer device for medical aerosol generators includes a body, fluidically coupled to a nebulizer and to a patient interface. An ambient air intake is formed into a lower body. The body is shaped and configured to optimize mixing of ambient air from the ambient air intake and the aerosol generated by the nebulizer, resulting in the formation of an aerosol plume having optimum characteristics for delivery of the aerosol to the patient's pulmonary system, such as the central or deep lung regions. The shape and dimensions of the body are further designed to minimize aerosol deposition, thus improving delivery efficiency.

8 Claims, 11 Drawing Sheets

Related U.S. Application Data continuation of application No. 14/040,277, filed on Sep. 27, 2013, now Pat. No. 9,144,650, which is a continuation of application No. 12/936,373, filed as application No. PCT/US2009/002054 on Apr. 2, 2009, now Pat. No. 8,555,874.

(60) Provisional application No. 61/123,133, filed on Apr. 4, 2008.

(51) Int. Cl.

| | | |
|---|---|---|
| *A61M 16/04* | (2006.01) | |
| *A61M 16/06* | (2006.01) | |
| *A61M 15/02* | (2006.01) | |
| *A61M 16/08* | (2006.01) | |
| *A61M 11/02* | (2006.01) | |
| *A61M 16/10* | (2006.01) | |
| *A61M 16/20* | (2006.01) | |
| *A61M 16/00* | (2006.01) | |

(52) U.S. Cl.
CPC .... *A61M 15/0018* (2014.02); *A61M 15/0085* (2013.01); *A61M 15/0086* (2013.01); *A61M 16/06* (2013.01); *A61M 16/085* (2014.02); *A61M 16/105* (2013.01); *A61M 16/20* (2013.01); *A61M 15/025* (2014.02); *A61M 16/04* (2013.01); *A61M 2016/0021* (2013.01); *A61M 2202/025* (2013.01); *A61M 2202/0208* (2013.01); *A61M 2202/0468* (2013.01); *A61M 2205/3386* (2013.01); *A61M 2205/50* (2013.01); *A61M 2205/75* (2013.01); *A61M 2205/8206* (2013.01); *A61M 2205/8262* (2013.01)

(56) References Cited

U.S. PATENT DOCUMENTS

| | | |
|---|---|---|
| 5,586,550 A | 12/1996 | Ivri et al. |
| 5,596,982 A | 1/1997 | Blaha-Schnabel |
| 5,758,637 A | 6/1998 | Ivri et al. |
| 5,922,675 A | 7/1999 | Baker et al. |
| 5,938,117 A | 8/1999 | Ivri |
| 6,014,970 A | 1/2000 | Ivri et al. |
| 6,085,740 A | 7/2000 | Ivri et al. |
| 6,129,080 A | 10/2000 | Pitcher et al. |
| 6,235,177 B1 | 5/2001 | Borland et al. |
| 6,467,476 B1 | 10/2002 | Ivri et al. |
| 6,540,154 B1 | 4/2003 | Ivri et al. |
| 6,546,927 B2 | 4/2003 | Litherland et al. |
| 6,629,646 B1 | 10/2003 | Ivri |
| 6,640,804 B2 | 11/2003 | Ivri et al. |
| 6,926,208 B2 | 8/2005 | Ivri |
| 6,968,840 B2 | 11/2005 | Smith et al. |
| 8,555,874 B2 | 10/2013 | Fink et al. |
| 9,144,650 B2 | 9/2015 | Fink et al. |
| 2002/0104531 A1 | 8/2002 | Malone |
| 2004/0084048 A1 | 5/2004 | Stenzler et al. |
| 2005/0217666 A1 | 10/2005 | Fink et al. |
| 2006/0137685 A1 | 6/2006 | Massardier et al. |
| 2014/0020680 A1 | 1/2014 | Fink et al. |

FOREIGN PATENT DOCUMENTS

| | | |
|---|---|---|
| WO | WO 03/089036 | 10/2003 |
| WO | WO 2006/084546 | 8/2006 |
| WO | WO 2006/095816 | 9/2006 |
| WO | WO 2006/098936 | 9/2006 |
| WO | WO 2006/127181 | 11/2006 |
| WO | WO 2009/042187 | 4/2009 |

OTHER PUBLICATIONS

PCT International Preliminary Report on Patentability corresponding to PCT Application No. PCT/US2009/002054 date of mailing Oct. 14, 2010.

AEROSOLIZATION DEVICE

CROSS REFERENCE TO RELATED APPLICATIONS

This application is a continuation of U.S. patent application Ser. No. 14/832,344, filed on Aug. 21, 2015, which is a continuation of U.S. patent application Ser. No. 14/040,277, filed on Sep. 27, 2013, now U.S. Pat. No. 9,144,650, which is a continuation of U.S. patent application Ser. No. 12/936,373, filed Dec. 23, 2010, now U.S. Pat. No. 8,555,874, which application is a national phase filing under 35 U.S.C. §371 of International Patent Application No. PCT/US2009/002054, filed Apr. 2, 2009, which claims the benefit of priority under 35 U.S.C. §119(e) to U.S. Provisional Patent Application Ser. No. 61/123,133, filed Apr. 4, 2008, all of which are incorporated herein by reference in their entireties.

BACKGROUND OF THE INVENTION

The present invention generally relates to systems and methods for the delivery of aerosolized medicaments. One or more embodiments of the invention relate to a device or system for the aerosolization and delivery of liquids, of liquid medicaments for safe, rapid and efficient delivery of the aerosolized liquids and liquid medicaments to the pulmonary system of a patient. More specifically, one or more embodiments of the invention relate to an aerosolization chamber for the transfer of an aerosolized medicament, and delivery of the aerosolized medicament to the pulmonary system of a patient.

Aerosolized medicaments can be administered directly to the lungs to treat diseases and/or conditions of the lung, and to treat diseases or conditions having a systemic effect or component thereof. Many medicaments cannot be administered orally, due to their sensitivity to metabolism and/or degradation and resulting inactivation in the gastrointestinal tract, thus pulmonary delivery avoids the need for intramuscular, subcutaneous or transdermal delivery and associated needles. Additionally or alternatively, it may be safer and/or more efficacious to deliver the medicament directly to the lungs and/or pulmonary system instead of other administration routes.

Moreover, when treating diseases and/or conditions of the lungs and/or pulmonary system, it is often safer and/or more efficacious to deliver the medicament directly to the lungs and/or pulmonary system, thereby avoiding or reducing the need for systemic administration of medicament.

Aerosolized medicaments are used to treat patients suffering from a variety of respiratory ailments. Medicaments can be delivered directly to the lungs by having the patient inhale the aerosol through a tube and/or mouthpiece coupled to the aerosol generator. By inhaling the aerosolized medicament, the patient can quickly receive a dose of medicament that is concentrated at the treatment site (e.g., the bronchial passages and lungs of the patient). Generally, this is a more effective and efficient method of treating respiratory ailments than first administering a medicament through the patient's circulatory system (e.g., intravenous injection). However, many challenges remain with the safe, efficient and efficacious delivery of aerosolized medicaments.

For example, delivery of aerosolized medicaments in the home may be limited by costly, bulky or difficult to operate equipment. Devices for delivery on large scale, such as vaccinations, are often costly and/or difficult to use in certain settings, such as remote and undeveloped areas.

Moreover, existing modes of administration are unsatisfactory for large-scale purposes. Injections are time-consuming, relatively costly and have significant compliance problems, particularly in developing countries. Oral administration is not suitable for many anti-infectives, and existing pulmonary administration methods suffer from one or more of requiring expensive and/or bulky equipment, long administration times, or contamination concerns.

The purpose of medical aerosol generator systems is to convert a medicated liquid or powder into aerosol form so that it can be administered to the airways of the respiratory tract. There are various commercially available medical aerosol generator systems in the form of pneumatically controlled, ultrasonic and vibrating-membrane devices in particular, as well as pressurized canisters with a metering valve.

The various published studies on this subject all agree and confirm that a large proportion of the dispensed aerosol is lost and wasted rather than being used for the desired therapeutic treatment. Authors and manufacturers alike estimate the proportion of aerosol that is actually used at approximately 25% (inhalable or available fraction). Losses are due to several parameters, including loss of the medication in the atmosphere when the patient exhales, the mass of medication lost in the nebuliser at the end of nebulisation and the mass lost during transfer of the aerosol.

According to U.S. Pat. No. 5,596,982 and WO 03/089036, for example, aerosol generators that use turbulence or vortex effects during transport of the aerosol are the cause of loss of aerosol particles. Obtaining this turbulence effect requires entry of air to take place in a plane that is perpendicular to the transport axis of the aerosol.

For these reasons, it's desirable to increase the aerosol delivery efficiencies of nebulizer systems. Embodiments of the present invention address these and other problems with conventional systems and methods of treating patients with aerosolized medicaments.

SUMMARY OF THE INVENTION

The present invention relates to the technical field of medical aerosol generator systems.

The present invention provides devices and methods for improving a level of safety to the patient and/or for providing an increased efficiency of delivery of an aerosol to the patient, and/or for providing aerosol delivery in a less expensive and/or more cost-effective manner.

References herein to "embodiment" or "embodiments" means one or more such embodiments, unless the context clearly indicates otherwise.

Embodiments of the invention provide treatments for a variety of ailments using a variety of aerosolizable medicaments. The ailments may include pulmonary ailments such as ventilator-associated pneumonia, hospital-acquired pneumonia, community-acquired pneumonia, asthma, cystic fibrosis, mycobacterial infection, mucociliary clearance conditions, bronchitis, staph infection, fungal infections, viral infections, tuberculosis, protozoal infections, emphysema, hereditary emphysema, Chronic Obstructive Pulmonary Disease (COPD) and acute exacerbation of COPD, among others. The aerosolizable medicaments used to treat the ailments may include antitrypsins (such as alpha-1 antitrypsin), antibiotics, anti-infectives, antivirals, anti-oxidants, epithelium sodium channel blockers, bronchodilators, beta-antagonists (short and long acting) corticosteroids, leukotrienes, protease inhibitors, surfactants, and vaccines, among other medicaments. The ailments may further include nonpulmonary-related, such as systemic conditions, such as diabetes, cancer, immune diseases, cardiovascular conditions, metabolic diseases and the like.

Embodiments of the invention include a method of treating a patient by administering to the patient a nebulized dose of aerosol comprising from about 0.5 mg to about 1000 mg (1 gm).

Embodiments of the invention about include a method of treating a patient by administering to the patient a nebulized dose of aerosol comprising from 0.05 mL to about 50 mL of a medicament.

Embodiments of the invention include methods of treatment by administering to a patient an aerosolized formulation comprising an anti-infective dissolved in an aqueous solution that is adjusted to a pH between about 5.0 and 8.5.

Embodiments of the invention include one or more methods of administering by nebulization wherein the medicament is administered continuously.

Embodiments of the invention include one or more methods of administering by nebulization wherein the medicament is administered intermittently.

Embodiments of the systems are configurable to administer aerosolized medicament, such as an anti-infective, to a freely-breathing patient.

Embodiments of the invention include one or more devices and methods of administering medicaments, such as an anti-infective, by nebulization wherein substantially all of the device is reused for multiple patients before disposing thereof.

Embodiments of the invention include one or more devices and methods of administering medicaments, such as an anti-infective, by nebulization wherein the device is used for only a single patient, then disposed.

Embodiments of the invention include one or more devices for administering medicaments, such as an anti-infective, by nebulization wherein some components of the device are reusable, and other components are disposable after a single use.

Embodiments of the invention include one or more methods of administering medicaments by nebulization wherein some components of the device are used for multiple patients before disposal of the component, and other components used for only a single patient.

Embodiments of the invention comprise a device which is small and portable, easy to transport, with low power requirements.

Embodiments of the invention also include a method of treating a patient with a pulmonary disease by administering to the patient a nebulized aerosol comprising from about 1 mg to about 500 mg of a medicament.

Embodiments of the invention still further include methods of treating a pulmonary disease by administering to a patient an aerosolized medicament comprising an antibiotic dissolved in an aqueous solution comprising sodium chloride that is adjusted to a pH between 5.0 and 6.3.

Embodiments of the invention include one or more methods of administering by nebulization using a vibratable member with apertures, the member configured to produce about 70% or more of aerosol particles with mass mean aerodynamic diameters from about 1 μm to about 7 μm.

Embodiments of the invention include one or more methods of administering by nebulization using a vibratable member with apertures, the member configured to produce about 60% or more of aerosol particles with mass mean aerodynamic diameters from about 1 μm to about 5 μm.

Embodiments of the invention include one or more methods of administering by nebulization wherein the medicament is administered continuously.

Embodiments of the invention include one or more methods of administering by nebulization wherein the medicament is administered intermittently.

Embodiments of the invention include one or more methods of administering by nebulization wherein the medicament is administered for a period of less than about thirty minutes.

Embodiments of the invention further include aerosolized medicament for the treatment of pulmonary disease. The medicament comprises aminoglycoside, such as amikacin.

Embodiments of the invention further include aerosolized medicament for the treatment of pulmonary disease. The medicament comprises glycopeptide, such as vancomycin.

Embodiments of the invention further include aerosolized medicament for the treatment of pulmonary disease. The medicament comprises surfactant.

Embodiments of the invention further include aerosolized medicament for the treatment of a pulmonary disease, wherein the medicament comprises an aqueous solution.

Embodiments of the invention further include aerosolized medicament for the treatment of pulmonary disease. The medicament comprises antitrypsin, such as alpha-1-antitrypsin.

Embodiments of the invention further include an aerosolized medicament for the treatment of systemic disease.

Embodiments of the invention still further include an aerosolized medicament comprising amikacin in an aqueous solution wherein the solution is preservative free.

Embodiments of the invention still further include an aerosolized medicament comprising vancomycin in an aqueous solution wherein the solution is preservative free.

Embodiments of the invention also provide for aerosolization and delivery of particular drug groups or drugs, such as, for example, antibodies, such as IgG or antibiotics, such as aminoglycosides, such as amikacin and/or glycopeptides such as vancomycin.

Embodiments of the present invention include one or more methods for adjunctive therapy, wherein an amount of medicament administered to a patient by means other than inhalation is reduced.

Embodiments of the present invention include one or more methods for adjunctive therapy, wherein an amount of antibiotic administered to a patient by means other than inhalation is reduced Embodiments of the present invention include one or more methods for adjunctive therapy, wherein the number of days a patient is required to receive a therapeutically-effective antibiotic, administered to a patient by means other than inhalation, is reduced.

Embodiments of the present invention include one or more methods for administration of aerosolized antibiotics to a patient wherein an antibiotic concentration in epithelial lining fluid, or tracheal aspirates, or both, exceeds a minimum inhibitory concentration for microorganisms usually responsible for Gram-negative pneumonia.

Embodiments of the present invention include one or more methods for administration of aerosolized antibiotics to a patient wherein an amikacin concentration in epithelial lining fluid, or tracheal aspirates, or both, exceeds at least about four times a minimum inhibitory concentration for microorganisms usually responsible for Gram-negative pneumonia.

Embodiments of the present invention include one or more methods for administration of aerosolized antibiotics to a patient wherein an antibiotic concentration in epithelial lining fluid, or tracheal aspirates, or both, exceeds a minimum inhibitory concentration for microorganisms usually responsible for Gram-positive pneumonia.

Embodiments of the present invention include one or more methods for administration of aerosolized antibiotics to a patient wherein an amikacin concentration in epithelial lining fluid, or tracheal aspirates, or both, exceeds at least about four times a minimum inhibitory concentration for microorganisms usually responsible for Gram-positive pneumonia.

Embodiments of the present invention include one or more methods for administration of aerosolized antibiotics to a patient wherein an antibiotic concentration in the lung and/or pulmonary system is present in a therapeutic-effective amount, and a need for systemically administered antibiotics is reduced.

Embodiments of the present invention include one or more methods for administration of aerosolized antibiotics to a patient wherein an antibiotic is dispersed into the deep lung and/or peripheral regions to provide a therapeutically-effective amount thereto.

Embodiments of the present invention include one or more methods for administration of aerosolized antibiotics to a patient wherein a drug is delivered with an efficiency of at least about 50%, or 55%, or 60%, or 65%, or 70%, or 75%, or 80%, or 85% or higher.

Further embodiments comprise any two or more of any of the foregoing features, aspects, versions or embodiments.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

It is to be understood that unless otherwise indicated the present invention is not limited to specific structural components, formulation components, drug delivery systems, manufacturing techniques, administration steps, or the like, as such may vary. In this regard, unless otherwise stated, a reference to a compound or component includes the compound or component by itself, as well as the compound in combination with other compounds or components, such as mixtures of compounds.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the electrode" includes reference to one or more electrodes and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

"Anti-infective" is deemed to include, antibiotics and antivirals, unless the context clearly indicates otherwise.

The term "efficiency" in the context of medicament delivery refers to the amount of solution containing medicament delivered to the target site in the pulmonary system, such as the lung and/or the deep lung.

Reference herein to "one embodiment", "one version" or "one aspect" shall include one or more such embodiments, versions or aspects, unless otherwise clear from the context.

As used herein, the terms "treating" and "treatment" refer to reduction in severity, duration, and/or frequency of symptoms, elimination of symptoms and/or underlying cause, reduction in likelihood of the occurrence of symptoms and/or underlying cause, and improvement or remediation of damage. Thus, "treating" a patient with an active agent as provided herein includes prevention or delay in onset or severity of a particular condition, disease or disorder in a susceptible individual as well as treatment of a clinically symptomatic individual.

The terms "disease" and "condition" are intended to be interchangeable, unless the context indicated otherwise.

As used herein, "effective amount" refers to an amount covering both therapeutically effective amounts and prophylactically effective amounts.

Fluid" means a liquid or a gas, or a combination thereof, specifically including an aerosol.

"Medicament" comprises any drug, agent, vaccine, compound, biological material which beneficially treats, prevents, helps to prevent, mitigates or alleviates any disease or condition, unless the context clearly indicates otherwise. "Active Agent" may be used interchangeably with "medicament".

As used herein, "therapeutically effective amount" refers to an amount that is effective to achieve the desired therapeutic result. A therapeutically effective amount of a given active agent will typically vary with respect to factors such as the type and severity of the disorder or disease being treated and the age, gender, and weight of the patient.

Each reference referred to herein, whether US or ex-US, publication, application or granted patent, or non-patent document, is incorporated herein in its entirety for all purposes.

The device according to the invention provides an aerosolization chamber or accumulator which is advantageous in that efficiency of delivery is thereby increased. Particles which comprise medical aerosols have a diameter of the order of one to seven micrometers in order to ensure they penetrate into and are deposited in the airways. Aerosol particles are thus suspended or dispersed in a gas (air) and are affected by the force of gravity. In a vertical chamber, the particles tend to fall due to the effect of their own weight (settling) until they encounter an obstacle and are deposited on it. In one or more embodiments, the present invention comprises using a vertical space to store the aerosol in order to limit deposition of particles by settling. In one or more embodiments, the space into which the aerosol is sprayed is sufficiently large such that the particles generated by the nebulizer are slowed down by air friction to a sufficient extent to limit their deposition when they impinge on the walls of the chamber. This also makes it possible to concentrate the aerosol during the phase when the patient exhales, thus increasing the quantity of the active agent or medicament inhaled each time the subject breathes in, thereby increasing the flow rate of the system. An aerosol transfer device for medical aerosol generators thus comprises a body, fluidically coupled to a nebulizer and to a patient interface. An ambient air intake is formed into a lower body. The body is shaped and configured to optimize mixing of ambient air from the ambient air intake and the aerosol generated by the nebulizer, resulting in the formation of an aerosol plume having optimum characteristics for delivery of the aerosol to the patient's pulmonary system, such as the central or deep lung regions. The shape and dimensions of the body are further designed to minimize aerosol deposition, thus improving delivery efficiency.

In one or more embodiments, the device has only a single valve.

In one or more embodiments, the device has two or more valves.

In one or more embodiments, the device is free of valves on the path the aerosol takes from the chamber to the patient.

In one or more embodiments, a volume of the chamber (reservoir) is less than a tidal volume of a targeted patient for whom the device and medication are intended.

In one or more embodiments, a volume of the chamber (reservoir) is large enough to hold a bolus of aerosol generated between inspirations without promoting condensation or increasing particle size, such as above about 7 microns.

In one or more embodiments, a length and width of the reservoir is greater than a length and width of the aerosol plume. This acts to minimize impaction of aerosol from plume on walls of the reservoir between breaths In one or more embodiments, the chamber (reservoir) may further comprise one or more baffles or turbulence producing features placed in inspiratory flow path to act as an impactor to remove large particles from aerosol prior to entering the upper airway.

In one or more embodiments, the chamber (reservoir) may further comprise one or more baffles or turbulence producing features in inspiratory flow path to reduce oral deposition to less than about 20% or 15% or 10%, or 5% or less, while not substantially reducing lung delivery.

DESCRIPTION OF THE DRAWINGS

These aspects and others will become apparent from the following description.

DETAILED DESCRIPTION

Figure 1:
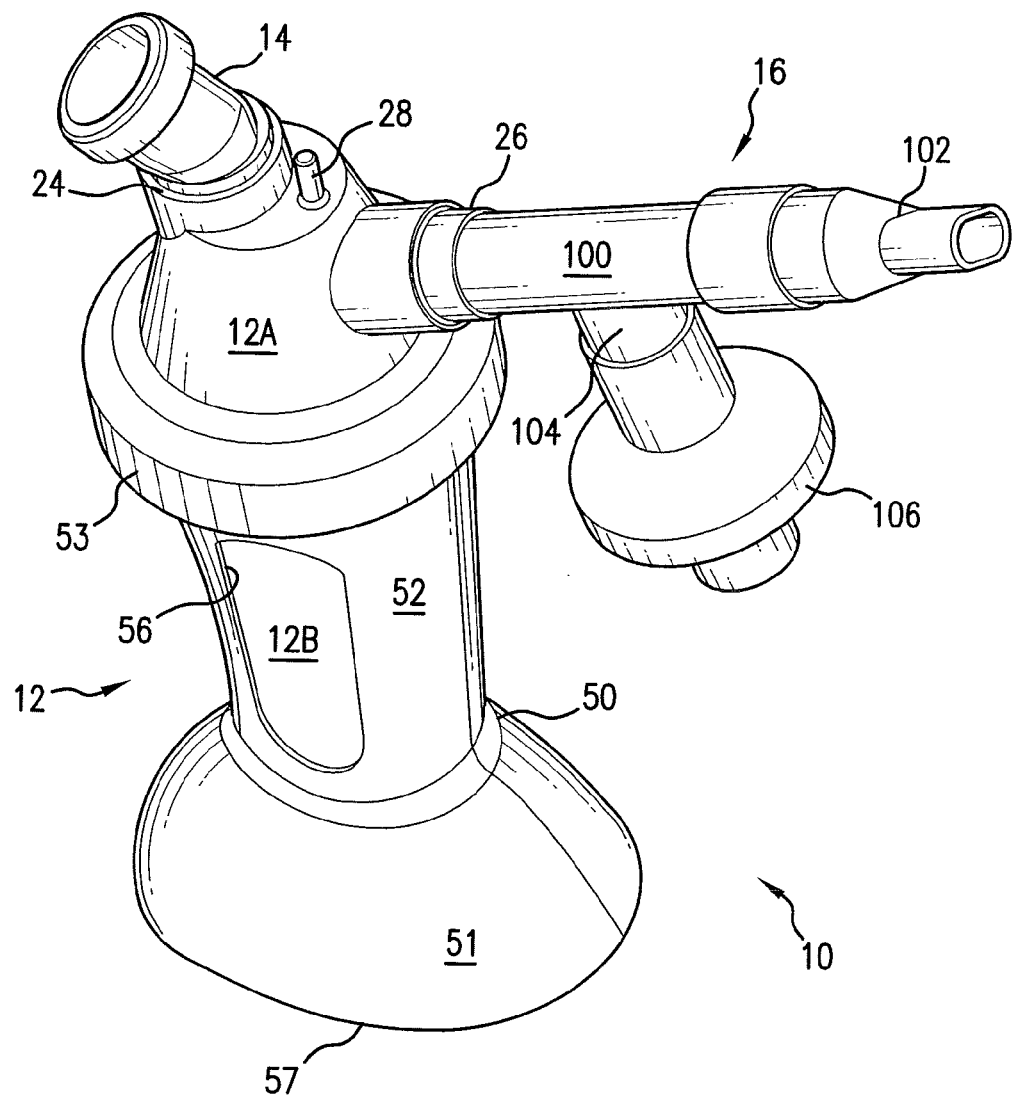
FIG. 1 is a perspective view of one embodiment of the aerosolization and aerosol transfer device of the present invention.
Figure 2:
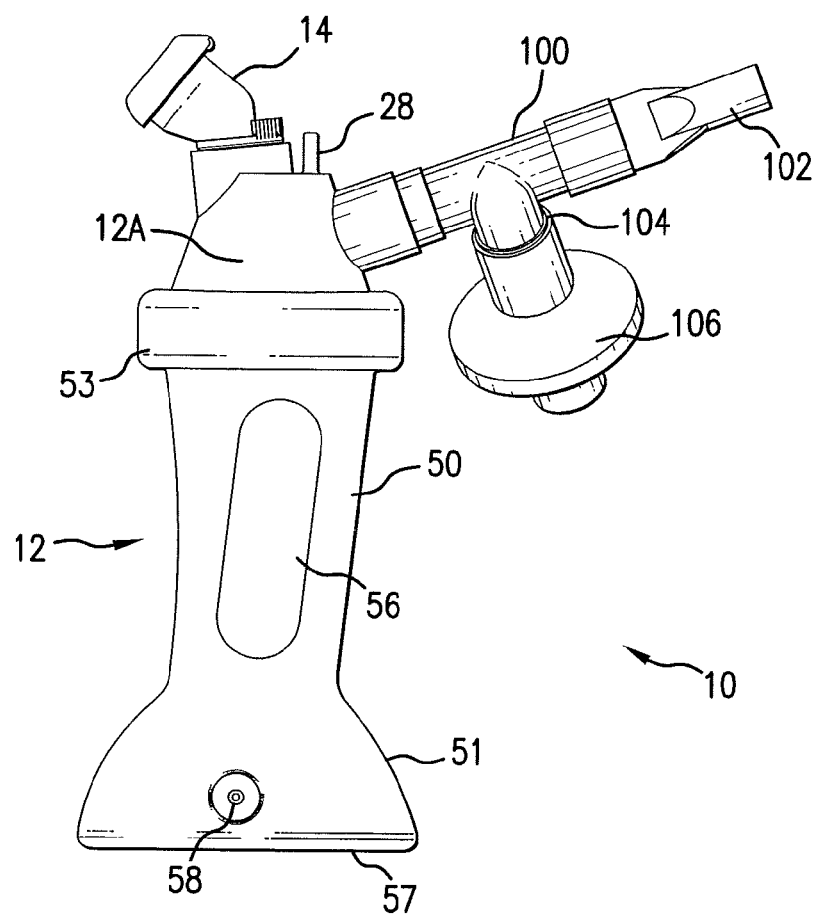
FIG. 2 is a side elevational view of one embodiment of the aerosolization and aerosol transfer device of FIG. 1.
Figure 3:
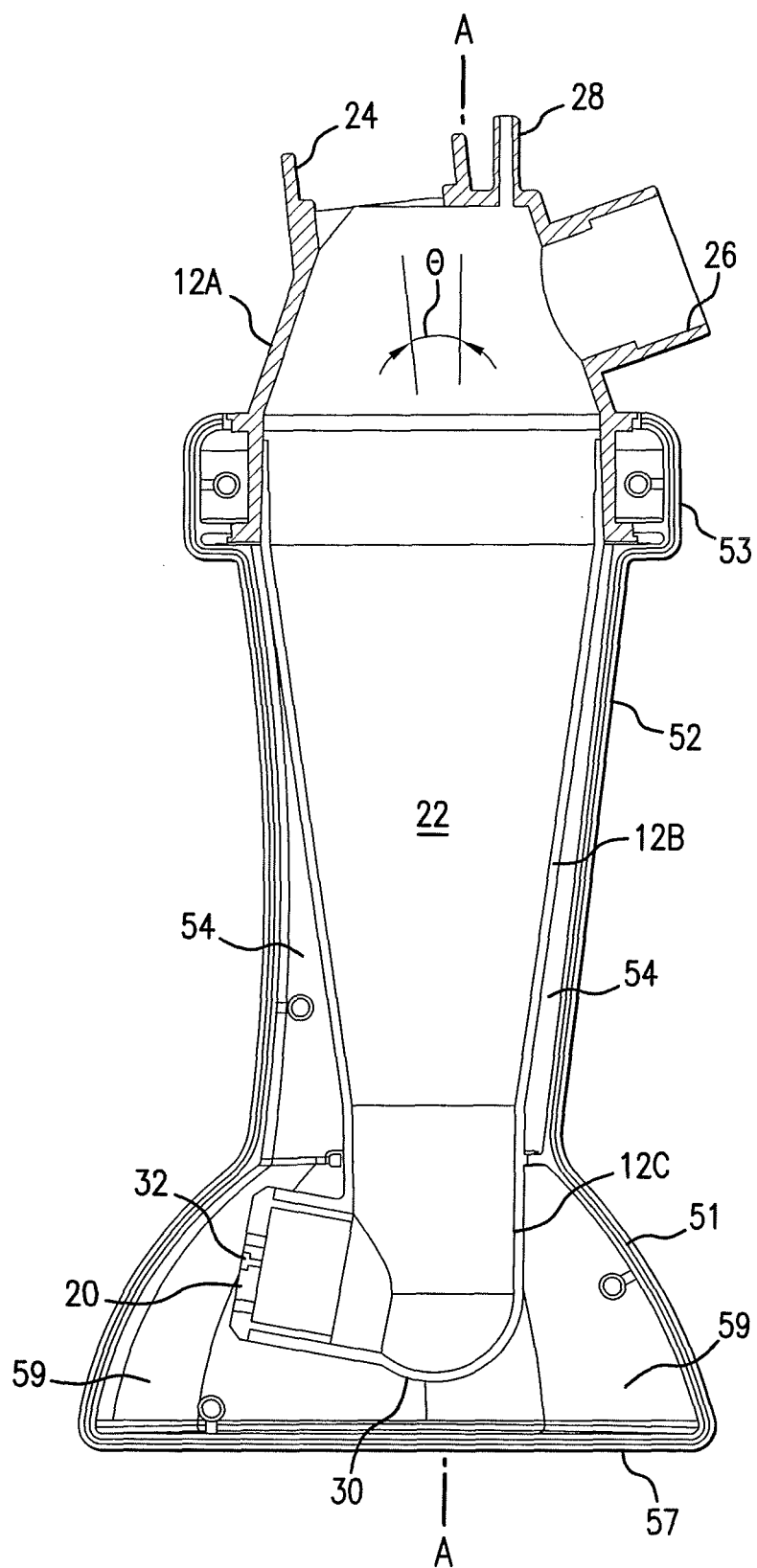
FIG. 3 is a partial side sectional view of one embodiment of the aerosolization and aerosol transfer device of FIG. 1.

An aerosolization transfer/accumulation system is shown in FIGS. 1-3 and identified by the general reference numeral 10. The system 10 comprises an aerosolization chamber or body 12 (also sometimes referred to herein as an accumulator), a nebulizer 14 and a patient interface 16. The nebulizer 14 comprises the source of aerosol which is thereby discharged into the body 12. The patient/aerosol generator interface 16 comprises the output for the generated aerosol, and is the means by which the aerosol is transported from the body 12 to the patient. As will be further described herein, the patient interface 16 may comprise a variety of structures, such as a mask, mouthpiece, hood, helmet, chamber, nosepiece, mechanical ventilator circuit, intubation catheter and tracheal catheter.

Figure 4:
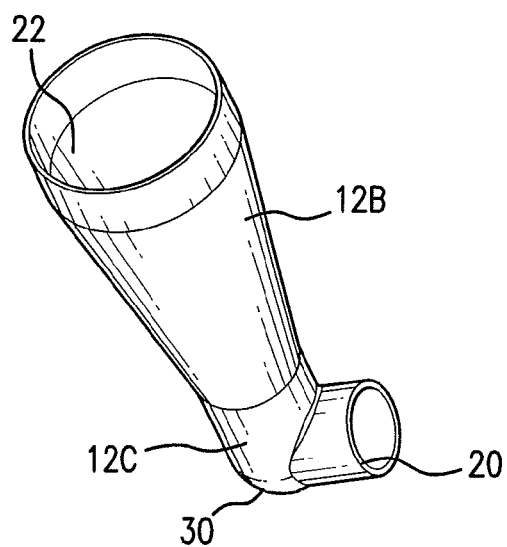
FIG. 4 is a perspective view of one embodiment of a subassembly of the aerosolization and aerosol transfer device of FIG. 1.

As illustrated in FIGS. 3 and 4, the body 12 may be conveniently subdivided into three components: an upper body 12A, and intermediate body 12B and a lower body 12C. In one or more embodiments of the upper body 12A is fluidically coupled to the nebulizer 14 (also sometimes referred to as an aerosol generator), and to the patient interface 16. In one or more embodiments, the lower body 12C comprises an ambient air inlet 20. In one or more embodiments, the intermediate body 12B fluidically connects the upper body 12A and the lower body 12C. The intermediate body 12B is shaped and configured to optimize mixing of ambient air from the inlet 20 and the aerosol generated by the nebulizer 14, resulting in the formation of an aerosol plume 21 (FIG. 5) having optimum characteristics for delivery of the aerosol to the patients pulmonary system, such as the central or deep lung regions. The shape and dimensions of the body 12B are further designed to minimize aerosol deposition in the system 10, thus improving delivery efficiency, as determined, for example by inhaled mass, and/or by target lung dose, and/or by pharmacokinetics. In one or more embodiments, the body 12 has a length, or a width, or both that is greater than the corresponding length, or width, or both of the aerosol plume 21.

It is to be noted that reference herein to the bodies 12A-12C is not to be construed as limiting to three discrete components, nor to exactly three components, nor to a particular order or arrangement of components. Rather, the references are illustrative only, and to aid in an understanding in one or more embodiments of the present invention, which includes other possible versions, alterations, permutations and equivalents of the embodiments shown, as will become apparent to those skilled in the art upon a reading of the specification. Furthermore, certain terminology has been used for the purposes of descriptive clarity, and not to limit the present invention.

In one or more embodiments, the body/accumulator 12 is generally symmetrical, having a central axis AA. In one or more embodiments, the axis AA forms an axis of rotational symmetry for the chamber 12, however the body/accumulator 12 may take on other forms of symmetry about axis AA, or may not be symmetrical thereabout.

Aerosol generated by the nebulizer 14 is delivered into an aerosolization chamber 22 (FIG. 3) defined by the bodies 12A, 12B and 12C. The body 12A is provided a nebulizer inlet port 24, and an aerosolized medicament outlet port 26 and may include a fluid control port 28 to which a fluid coupling may be connected.

Air is admitted via aperture 20 into the chamber 22 and thereby entrains the aerosolised medicament generated by the nebulizer 14. The air/medicament aerosol mixes in the chamber 22, and which is then delivered to the patient through the aerosolized medicament outlet port 26 via the patient interface device 16.

The bodies 12A and 12B comprise chambers which are generally conically-shaped, or tapered, and in one or more embodiments are frusto-conical. In one or more embodiments the bodies 12A and 12B collectively comprise a conjoined double frustroconical shape, also known as a bifrustum. In one or more embodiments the chamber 22 may have a ratio of maximum diameter to minimum diameter of about 5:4 to 2:1.

The bodies 12A, 12B and 12C may be formed as a unitary piece, or each may be formed individually and sealed or attached in an abutting fashion by any means known to the art, such as by adhesive, ultrasonic welding, and the like. The bodies 12A or 12B may additionally be formed to have integral sealing means such as screw threads, bayonet threads or other releasable locking means. In some embodiments, the bodies 12A or 12B may be self assembled and/or disassembled as well.

The body 12C comprises a generally tubular component, at its upper end abutting with, and fluidically coupled to, the intermediate body 12B, and having at a lower apex thereof an elbow joint 30 projecting generally perpendicularly from the longitudinal axis AA of the accumulator 12. In one or more embodiments, the elbow joint 30 is configured to position the inlet 20 to admit air in a direction that is non-aligned with the axis AA. In one or more embodiments, the inlet 20 may thus be orthogonal to the axis AA, or may be nearly aligned therewith. If nearly aligned, the inlet 20 may be offset from the axis AA so that air flow is not coaxial therewith. In one or more embodiments, the inlet 20 may be oriented to be from about 1° to about 145° with respect to the axis AA. The elbow joint 30 terminates in the air inlet 20, and may be terminated by an inlet valve 32, which allows ambient air into the body 12 to mix with the medicament aerosol generated, thereby providing the appropriate mixture of air and medication for the patient. The valve 32 beneficially prevents exit of gases from the chamber 22, such as during exhalation by the patient. The valve 32 may comprise a silicone flap-type valve, a coaxial valve or a fluidic valve. Additionally or alternatively, in some embodiments the valve 32 may be omitted entirely, and replaced by a fixed orifice (not shown) or by an orifice covered by a porous membrane or filter-type material.

In one or more embodiments, the body 12C and elbow joint 30 are configured to have a curved surface at the lowest point thereof. In other words, the lower end is concave (from the point of view of the aerosol) and is the lowest point of the joint 30. This concavity aids in limiting aerosol deposition by settling, also known as sedimentation.

The chamber 22 has a major dimension, i.e. a length or a diameter. The major dimension may be 8 or 9 or 10 or 11 or 12 or 13 or 14 or 15 or 16 or 17 or 18 or 19 or 20 or 21 or 22 or 23 or 24 or 25 cm. Referring to the chamber 22 formed by a frustroconical, or bifrustoconical body 12, the length of the body 12 (along the axis AA) may vary, as may the diameter of the chamber 12 at its widest point, and/or at its narrowest point, or both. In one or more embodiments, the chamber 22 is approximately 5 to 8 cm wide at a maximum, and tapers to approximately 2 to 3 cm at its narrowest width. Referring to the chamber 22 formed by a frustroconical, or bifrustoconical body 12, the major dimension comprises a length of the body 12 (along the axis AA) which may comprise a vertical dimension of about 8 to 25 cm, such as about 10 to 22 cm or about 14 to 20 cm, or any combination thereof.

The fluid coupling port 28 permits tubing to be attached to the accumulator 12 in order to measure and/or to control various fluidic parameters. For example, a pressure sensor (not shown) may be fitted to the port 28 and used to measure breathing characteristics, which characteristics may then be used to control nebulization. In one or more embodiments, additional openings, ports or apertures (not shown) may optionally be formed in the body 12A to admit a secondary gas and/or to exhaust a gas or gases. Said other optional openings may also accommodate valves and any other kinds of active or passive connections which are useful for the aerosol session. The system 10 may also be fitted with additional port and/or fluid couplings to permit addition of other gasses, such as oxygen, and/or to measure or sample patient breathing characteristics and/or gases.

Referring also to FIG. 3, the bodies 12B and 12C are partially enclosed by a shell, 50 which may be generally partially congruent in shape with the body 12B. In one or more embodiments, the shell 50 is comprised of two sections: a base section 51 and an upper shell portion 52. In one or more embodiments, an annular collar 53 may help to secure the upper shell portion 52 to the upper body 12A. The shell 50 is configured and dimensioned such that there is a plenum 54 (FIG. 3) defining an air/gas passage intermediate to the shell 50 and the body 12. This plenum 54 allows drawing in air external to the device 12 and consequent mixing of air with aerosol in the chamber 22. Air is admitted into the chamber 22 through the plenum 54 via one or more apertures 56 around the periphery of the outer shell 50. The apertures 56 are preferably along the axis of the storage area, i.e. in a vertical plane. In one or more embodiments, there are two diametrically opposed apertures 56. In one or more embodiments, each of the two apertures 56 comprise an inlet area of about 6 to 20 cm$^2$, such as 8 to 18 cm$^2$ or about 10 to 15 cm$^2$. In one or more embodiments, there may be three or more apertures 56 spaced equally, or non-equally about a periphery of the shell 50. In conjunction with the air inlet 20 located on the lower portion of the body 12C, intake air flow from the apertures 56 aids in limiting turbulence and vortex effects which can cause loss of particles, e.g. through impaction and/or sedimentation.

The base 51 may provide for a convenient means of stably resting the device 12 on a surface. The exact shape and dimensions of the base 51 may vary and may comprise a variety of shapes. In one or more embodiments the base 51 comprises a generally hemispherical or bowl shaped portion with a flat bottom 57. Formed within the base 51 may be a port or ports 58, which maybe connectable to a gas line, such as an oxygen line to enrich the oxygen content of the air flowing in to the chamber 12 via the apertures 56. An internal space formed by the base 51 may comprise an oxygen accumulation reservoir 59, which functions to ensure a steady supply of enriched oxygen to the patient when an oxygen source is coupled to the port 58.

Figure 5:
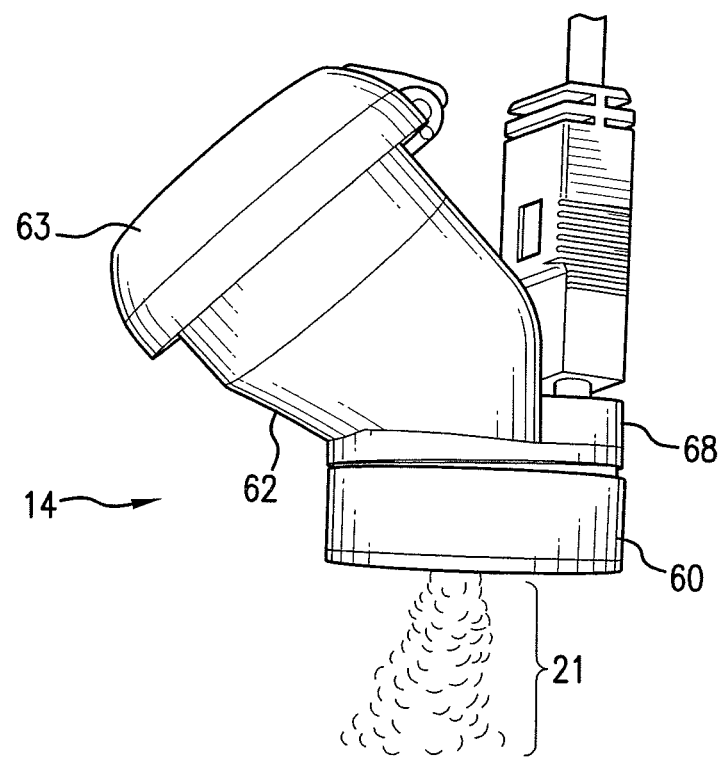
FIG. 5 is a perspective view of one embodiment of an aerosol generator of the system of present invention.
Figure 6:
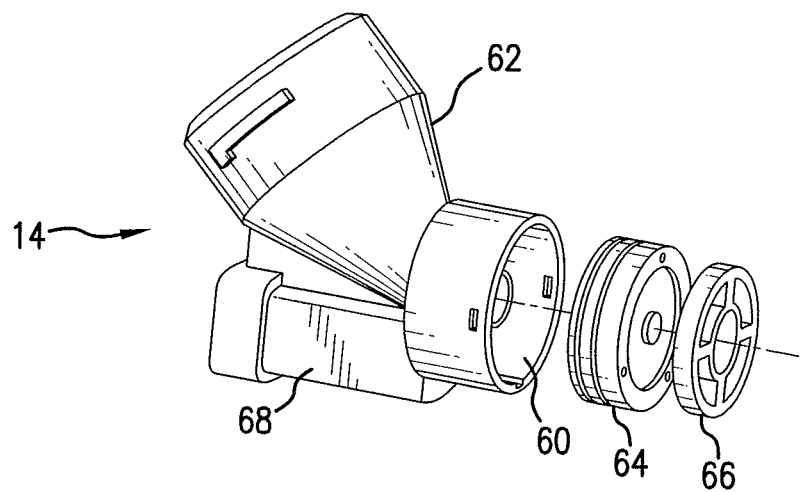
FIG. 6 is a perspective, exploded view of one embodiment of the aerosol generator of FIG. 5.

The nebulizer port 24 is dimension and sized to accept a nebulizer, especially a vibrating mesh nebulizer. In particular, the nebulizer port 24 is dimensioned and sized to accept a vibrating mesh nebulizer 14 as manufactured by Aerogen, Inc. {Galway, Ireland) and having a vibrating mesh aerosolization engine, comprising a dome-shaped aperture plate and a piezoelectric ring, which vibrates the aperture plate at a very high rate, forcing liquid through apertures in the plate to yield a fine and consistent particle size. Referring to FIGS. 5 and 6, the nebulizer 14 comprises a housing 60, and also comprises a reservoir 62, which may be sealed by a cap 63. The nebulizer 14 as well comprises an aerosol generator, or aerosolization element 64, which may be retained within the housing 60 by a internal generally coaxial annular retainer 66. In some embodiments, the aerosolization element 64 may be supported within the nebulizer housing 60 by any means known to the art such as adhesives, mechanical, securing means such as tabs flanges etc. In some embodiments, an elastomeric O-ring may placed adjacent to the aerosolization element 64 to dynamically isolate it within the nebulizer 14.

In one or more embodiments, the nebulizer 14 slip fits into the nebulizer port 24, and is held therein by frictional engagement. This permits discarding the nebulizer 14 while reusing the remainder of the device 12. The nebulizer 14 may thus be configured as single use, or may be used multiple times. If single use, the nebulizer 14 may further be configured to be pre-supplied with a medicament to be aerosolized. Similarly, the device 12 (and/or system 10) may be single use, or multiple use.

An electrical connection port 68 is formed within a portion of the housing 60 and provides a conduit for an electrical connection for a control and power supply means. Further examples of nebulizers 14 and methods of use thereof may be found in U.S. Pat. Nos. 5,164,740; 5,586,550; 5,758,637; 6,085,740; 6,467,476; 6,640,804; 6,629,646; 6,926,208; and 6,968,840, the full disclosures of which are incorporated by reference herein.

Figure 7:
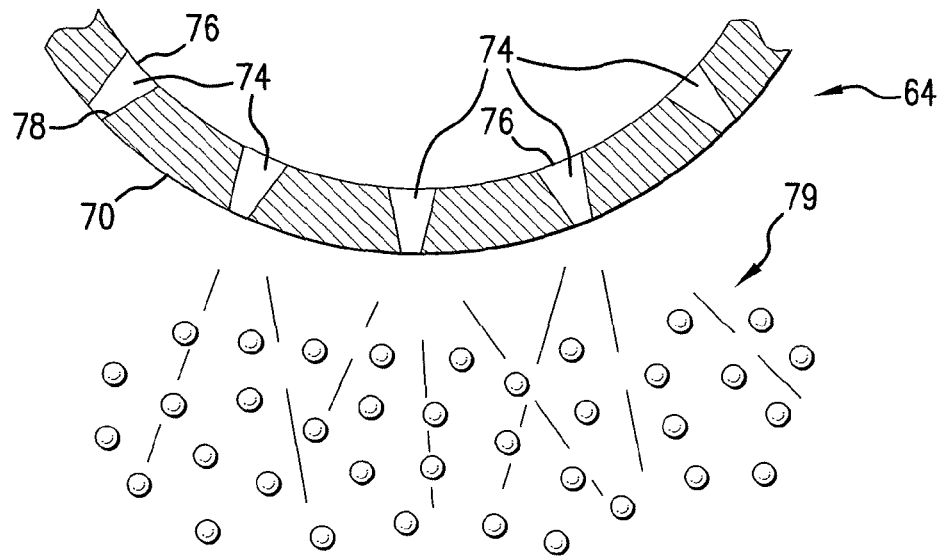
FIG. 7 is a magnified, schematic side sectional view of one embodiment of an aerosol generator of the device of the present invention.
Figure 8:
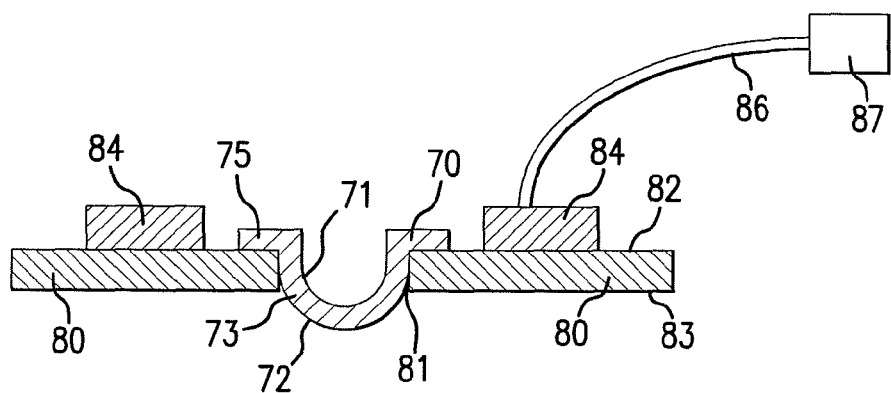
FIG. 8 is a magnified, schematic side sectional view of one embodiment of an aperture plate of the aerosol generator of FIG. 7.

Referring now to FIGS. 7 and 8, in one or more embodiments, the aerosolization element 64 comprises an aperture plate 70 which may be configured to have a curvature, as in a dome shape, which may be spherical, parabolic or any other curvature. The aperture plate 70 may be formed to have a dome portion 73, and this may be concentric with the center of the aperture plate 70, thus leaving a portion of the aperture plate 70 that is a substantially planar peripheral ring portion 75. The aperture plate 70 has a first face 71 and a second face 72. The aperture plate 70 may also have a plurality of apertures 74 therethrough. The first face 71 may comprise the concave side of the dome portion 73 and the second face 72 may comprise the convex side of the dome portion 73 of the aperture plate 70. The apertures 74 may be tapered to have a wide portion 76 at the first face 71 and a narrow portion 78 at the second face 72 of the aperture plate 70. Typically, a liquid will be placed at the first face 71 of the aperture plate 70, where it can be drawn into the wide portion 76 of the apertures 74 and emitted as droplets 79 (forming the plume 21) from the narrow portion 78 of the apertures 74 at the second face 72 of the aperture plate 70.

The aperture plate 70 may be mounted on an aerosol actuator 80, which defines an aperture 81 therethrough. This may be done in such a manner that the dome portion 73 of the aperture plate 70 protrudes through the aperture 81 of the aerosol actuator 80 and the substantially planar peripheral ring portion 75, on the second face 72 of the aperture plate 70 abuts a first face 82 of the aerosol actuator 80. A vibratory element 84 may be provided, and may be mounted on the first face 82 of the aerosol actuator 80, or alternatively may be mounted on an opposing second face 83 of the aerosol actuator 80. The aperture plate 70 may be vibrated in such a manner as to draw liquid through the apertures 74 of the aperture plate 70 from the first face to the second face, where the liquid is expelled from the apertures as droplets 79. The aperture plate 70 may be vibrated by the vibratory element 84, which may be a piezoelectric element. The vibratory element 84 may be mounted to the aerosol actuator 80, such that vibration of the vibratory element 84 may be mechanically transferred through the aerosol actuator 80 to the aperture plate 70. The vibratory element 84 may be annular, and may surround the aperture 81 of the aerosol actuator 80, for example, in a coaxial arrangement.

A circuitry 86 may provide power from a power source. The circuitry 86 may include a switch means or element that may be operable to vibrate the vibratory element 84 and thus the aperture plate 70, and aerosolization performed in this manner may be achieved within milliseconds of operation of the switch means. The circuitry 86 may include a controller 87, for example, a microprocessor that can provide power to the vibratory element 84 to produce aerosol from the aperture plate 70 within milliseconds or fractions of milliseconds of a signal to do so. For example, aerosol production may begin within about 0.02 to about 50 milliseconds of such a signal and may stop within about 0.02 to about 50 milliseconds from the cessation of a first signal or a second signal either of which may act as a trigger to turn of aerosolization. Similarly, aerosol production may begin and end within about 0.02 milliseconds to about 20 milliseconds of such respective signaling. Likewise, aerosol production may begin and end within about 0.02 milliseconds to about 2 milliseconds of such respective signaling. Further, this manner of aerosolization provides full aerosolization with a substantially uniform particle size of low velocity aerosol plume 21 being produced effectively instantaneously with operation of the switch means or element.

In one or more embodiments, the aerosol plume 21 is low velocity. In one or more embodiments, the aerosol plume 21 has an initial velocity (immediately downstream of the aerosol generator 14) of between about 0.5 and 8 meters per second (m/s). Typically, such a plume decelerates rapidly after generation.

The switch means, described above, may be operable by a pressure transducer, which may be positioned in the mouthpiece of the nebulizer. The pressure transducer may be in electrical communication with the circuitry, and a microprocessor may also be in electrical communication with the circuitry, and the microprocessor may interpret electrical signals from the pressure transducer, and may also operate the switch to begin aerosolization. In this manner, nebulization can begin substantially instantaneously with the inhalation of a user upon the mouthpiece. An example of such a sensor switch can be found in co-assigned PCT Publication No. WO2002/036181, the entire contents of which is hereby incorporated herein by reference.

A transducer (not shown) may be used to sense the absence or presence of liquid in the reservoir, by sensing, for example, a difference between vibration characteristics of the aerosolization element, such as, for example, differences in frequency or amplitude, between wet vibration and substantially dry vibration. In this manner, the circuitry, may, for example by way of the microprocessor, turn the vibration off when there is essentially no more liquid to aerosolize, i.e., when the end of the dose has been achieved, thus minimizing operation of the aperture plate 70 in a dry state. Likewise, the switch means may prevent vibration prior to delivery of a subsequent dose into the reservoir. An example of such a switch means or element is shown in co-assigned U.S. Pat. No. 6,546,927, the entire contents of which is hereby incorporated herein by reference.

In one or more embodiment, the aerosol generator is switched on to commence nebulization, and remains on until the liquid in the reservoir is nebulized, whereupon it is switched off. The switching on and off may be accomplished manually by the user, or by appropriate sensors (such as breathing sensors and/or liquid level sensors) or by a combination of such means. In one or more embodiments, a controller is provided which allows manual actuation of the aerosol generator, however, further limited by a breathing sensor, such that nebulization only occurs while breathing is detected (thus if the patient disengages form the patient interface, nebulization stops). The controller further may include a sensor means for stopping nebulization once the reservoir is exhausted.

In one or more embodiment, the aerosol generator is controlled by an electronic controller as described in greater detail in U.S. Pat. Nos. 6,540,154, 6,546,927 and 6,968,840 and US Patent Application Publication 2005/0217666, published Oct. 6, 2005. In one or more embodiments, it is sufficient that the controller supply power to the piezoelectric generator and to switch generation of the aerosol on and off between patients. In other embodiments, the controller may supply power and switch the aerosol generator 14 on and off according to a predefined protocol or according to measured or calculated breathing characteristics, or both. For example a pressure sensor (not shown) may be fitted to port 28 in the nebulizer body 12, and used to measure breathing characteristics.

The pressure in the apparatus may be monitored throughout the breathing cycle with a pressure sensor coupled to fluid control port 28. The pressure sensor (not shown) may generate an analog or digital electronic signal containing information about the pressure level in the apparatus. This signal may be used to control the amount of aerosolized medicament and/or gases entering the apparatus over the course of the patient's breathing cycle. For example, when the pressure in the apparatus decreases as the patient inhales, the pressure signal may cause the nebulizer 14 to add aerosolized medicament to the apparatus, and/or cause the gas source or pump to add gas into the chamber 59. Then, when the pressure in the apparatus increases as the patient exhales, the pressure signal may cause the nebulizer 14 to stop adding aerosolized medicament to the apparatus, and/or cause the gas source or pump to stop adding gas into chamber 59.

In one or more embodiments the droplets 79 are between about 0.5 and 10 microns in size. In one or more embodiments, the droplets 79 are greater than about 1 or 2 or 3 or 4 or 5 microns. In one or more embodiments, the droplets 79 are smaller than about 10 or 9 or 8 or 7 or 6 microns. In one or more embodiments, about 70% or more (by weight) of the droplets 79 have sizes from about 1 to about 7 microns, or about 1 to about 6 microns. In one or more embodiments, about 50% or 60% or 70% or 75% or more (by weight) of the droplets 79 have sizes from about 0.5 to about 7 microns, or about 1 to about 6 microns. In one or more embodiments, about 50% or 60% or 70% or 75% or more (by weight) of the droplets 79 have sizes from about 3 to about 6 microns.

In one or more embodiments the controller may comprise a battery operated unit. Additionally or alternatively, the controller may connect directly to a mains power source. In this case the controller would have has an integral AC-DC circuit (not shown) as well as control circuitry (not shown) mounted in a single housing. In one or more embodiments electrical connections to supply power to, and to control vibration of the vibratory element 84 are achieved by any means known in the art such as by direct electrical connection, wireless coupling, or any other means by which current and voltage can be supplied to the vibratory element 84. Power may be supplied from an electrochemical cell or cells, line current, or any other source. The low power requirements (about 1-3 watts) of the device make it well suited for uses in remote area wherein power is not readily available. The device can thus advantageously be powered also by internal sources, such as small batteries, or local external sources such as solar, wind, small hydroelectric, or manually-generated (e.g. hand cranked) power.

The nebulizer 14 is contained within the body 12, and in one or more embodiments, as shown, for example, in FIG. 1 is positioned to manner that directs the aerosol plume cloud 21 downwardly into body 12B. In one or more embodiments, the nebulizer 14 may be offset from, and/or angled with respect to the central axis AA. However, it is noted that the nebulizer 14 may be generally coaxial therewith as well. In one or more embodiments, the nebulizer 14 is positioned such that aerosol generated thereby does not re-circulate and impact on any portion or wall of the body 12 defining the chamber 22, or settle (sediment) onto the elbow 30. The nebulizer 14 may also be positioned in the port 26, with the patient interface 16 then positioned in the complementary port 24. In one or more embodiments, the shape of the body 12, such as a frustoconical or bifrustrum, is configured and dimensioned to minimize or prevent impaction and/or sedimentation.

In one or more embodiments, the chamber 22 contains aerosol during nebulization, and upon inspiration gas (air and/or oxygen) is drawn through the chamber 22 allowing a bolus of aerosol to enter the patient's airway. In one or more embodiments, the nebulizer 14 (and/or the aerosolization element 64) is positioned to generate and direct the aerosol plume 21 at an angle θ (theta) relative to the vertical axis AA. The angle .theta. may be about 1° to about 45°, such as about 5° to 10°. The angle .theta. is selected to help minimize impaction and/or sedimentation losses.

Exemplary Nebulizers

In regard to the nebulizers (i.e., aerosol generators), they may be of the type, for example, where a vibratable member is vibrated at ultrasonic frequencies to produce liquid droplets. In one or more embodiments, the ultrasonic frequency of vibration comprises at least about 45 kHz. Some specific, non-limiting examples of technologies for producing fine liquid droplets is by supplying liquid to an aperture plate having a plurality of tapered apertures and vibrating the aperture plate to eject liquid droplets through the apertures. Such techniques are described generally in U.S. Pat. Nos.

5,164,740; 5,938,117; 5,586,550; 5,758,637, 6,014,970, and 6,085,740, the complete disclosures of which are incorporated by reference. In one or more embodiments of the present invention, the aerosol generator comprises a vibrating mesh type, wherein vibrational energy is supplied via a piezoelectric element in communication (directly or indirectly) with the mesh element. In particular, a suitable aerosolization body 12 is dimensioned and configured to accept a vibrating mesh aerosol generator 14 as manufactured by Aerogen, Inc. having a vibrating mesh aerosolization engine, comprising a dome-shaped aperture plate and a piezoelectric ring, which vibrates the aperture plate at a very high (ultrasonic) rate, forcing liquid through apertures in the plate to yield a fine and consistent particle size. However, it should be appreciated that the present invention is not limited for use only with such devices.

The aperture plate 70 may be constructed of a variety of materials, comprising metals, which may be electroformed to create apertures as the element is formed, as described, for example, in U.S. Pat. No. 6,235,177 assigned to the present assignee and incorporated by reference herein in its entirety. Palladium is believed to be of particular usefulness in producing an electroformed, multi-apertured aerosolization element, as well as in operation thereof to aerosolize liquids. Other metals that can be used are palladium alloys, such as PdNi, with, for example, 80 percent palladium and 20% nickel. Other metals and materials may be used without departing from the present invention.

In one or more embodiments, the nebulizer 14 and controller 87 comprise a system known as a Pulmonary Drug Delivery System (PDDS) manufactured and sold by Stamford Devices Ltd., Galway, Ireland (Formerly Aerogen, Inc. of Mountain View, Calif.). The PDDS system is more fully described in previously-referenced US Patent Application 2005/0217666, assigned to Aerogen, Inc.

In one or more embodiments, the aerosol generator comprises a tube core configuration, as described in WO 2006/127181, assigned to the same assignee as the invention herein.

The patient interface device 16 may be durable and reusable, or disposable. Generally a single patient interface device will be disposable, however, a disposable patient interface device may also be used for multiple patients prior to disposing. Similarly, a durable patient interface device 16 may be used for a single patient, then discarded. The patient interface device 16 is fluidically coupled to the aerosol outlet port 26. In one or more embodiments, and referring to FIGS. 1 and 2, the patient interface device 16 comprises a tubular conduit 100 and a mouthpiece 102. In one or more embodiments, the port 26 is capable of accepting a standard patient mouthpiece, lip seal or mask for delivery of the aerosolized medicament to the pulmonary system and/or lungs of the patient. In one or more embodiments, the port 26, and correspondingly, conduit 100 are angled upwardly by about 20° relative to the horizontal (or about 110° relative to axis AA). In one or more embodiments, an aerosolized dose of medication may require about 10 to 60 seconds to administer. During administration, the patient typically breathes multiple times, such as about 10-40 times per minute, thus multiple inspiration and expiration cycles take place while the medication is being aerosolized and administered. For this reason, in one or more embodiments it is preferable to incorporate one or more exhaust port(s) 104 into the nebulizer body 12 to permit the exhaustion of exhaled air from the patient.

In one or more embodiments, the exhalation exhaust port 104 is located in the conduit 100 at a point intermediate to the aerosol outlet port 26 and patient interface device 16. In one or more embodiments, a filter 106 is fitted to the exhaust port 104. The filter 106 may comprise any filter for filtering out extraneous aerosolized medicament, such as a membrane or depth type filter, and may be made of any suitable filter material such as polymeric membranes, porous plastic, sintered porous plastic, filter paper, woven or nonwoven fabric, textile or paper material. Additionally, or alternatively, the exhaust port 104 may further comprise a valve (not shown), substantially as described in respect of inlet valve 32. In preferred embodiments, an orientation of the exhaust port 104 and filter 106 (if present) is other than straight down, i.e. it should not be in a vertical (downward) orientation. In one or more embodiments, an orientation of the exhaust port 104 and filter 106 (if present) is from about eighty-five degrees downward from the horizontal to about ninety degrees upward. In other words, if viewed from an axis extending through the center of rotation of conduit 100, the orientation of the exhaust port 104 and filter 106 (if present) could describe an arc of about 350 degrees, the exception being the lower ten degrees of arc. Preferably, the orientation of the exhaust port 104 and filter 106 (if present) is such that there is some upward component thereto.

In one or more embodiments, the exhaust port or ports 104 may comprise a simple fixed orifice or orifices (also known as a resistor, in reference to the orifice's resistance to flow, absent a valve) formed into a circumference of the conduit 100, with the filter 106 omitted. In one or more embodiments, the port or ports 104 are fitted with an exhalation filter element, comprising a band of filter material encircling the portion of the conduit 100 containing the port or ports 104. In one or more embodiments, the filter element may be sized and positioned to cover only an individual port or ports 104. The filter element comprises a membrane or depth type filter, and may be made of any suitable filter material as described above. Such a filter element is more fully described in co-pending and co-assigned U.S. Patent Application No. 61/068,577, filed Mar. 7, 2008, the entire contents of which are incorporated herein by reference.

In one or more embodiments, the dimensions, size and/or shape of the port 104, and/or the dimensions, size and/or shape of the port 104 coupled with the filter 106 and/or a covering filter element provides sufficient impedance to prevent loss of aerosol during inhalation. As the patient inhales, the inlet valve 32 opens, allowing air to mix with the downward-forming aerosol plume 79 in the chamber 22. As the patient continues to inhale, the mixture travels up to and through body 12A, and into the patient's pulmonary system via the conduit 100 and mouthpiece 102. The port 104 and/or filter 106 and/or a filter element continue to prevent escape of aerosol during this step. As the patient exhales, the exhalation pressure is sufficient close inlet valve 32, and to overcome the impedance of port 104 and/or filter element 106, and exhalation gases are thus expelled through the exhaust port 104. In one or more embodiments, it has been found that a round port 104, having a diameter of about 3 or 4 or 5 or 6 or 7 mm, is preferred. In one or more embodiments, a plurality of ports 104 are provided, and each port may have a size of about 1 or 2 or 3 or 4 mm.

In one or more embodiments, the exhaust port or ports 104 may comprise an orifice with valve or multiple orifices with valves. In one or more embodiments, the exhaust port or ports 104 may comprise a combination of one or more fixed orifices and one or more orifices with valve. The valve or valves may be silicone flap-type valve, coaxial valve or fluidic valve as described herein.

Table 1 below shows aerosol characteristics for three different sizes of port 104. Percentage of inhaled mass is a measured quantity, and represents the amount of aerosolized medicament which would be inhaled by a patient. Chamber percent is measured and represents the amount remaining in the chamber 22. MMAD is the mass median aerodynamic size of the aerosolized droplets 79, and FPF.sub.<5 µm denotes the fine particle fraction under 5 microns, which represents a particle size distribution well suited for delivery to the deep lung. Inhaled mass may be measured by a variety of means, such as by scintigraphy, or by washing the device or component thereof, eluting the drug and directly measuring, e.g. by titration. Inhaled mass measurements are described, for example, in European Standard EN13544-1, which is incorporated by reference herein.

TABLE-US-00001 TABLE 1 Exhalation Port Diameter 4 mm 5 mm 6 mm Inhaled Mass % 80.4 80 78 Chamber % 8 7 9 MMAD (µm) 3.4 3.4 3.4 FPF<5 µm 72% 71% 72%

The device 10 generally is comprised of any material which is sufficiently durable to withstand handling, non-reactive to the medicaments, and which can be readily cleaned and sterilized, where the device is intended for re-use. Preferred are polymeric materials such as acrylics, or biodegradable plastics, or naturally-occurring materials such as paper, the latter materials intended for disposable components.

It is also within the scope of the present invention to form either or both the bodies 12A or 12B as a cylindrical shape, a conical shape, a simple columnar shape, a globe shape, a combination column with globe shape, a spiral channel shape, a pear shape, a peanut shape, a tear drop shape, a gourd shape, and combinations thereof. In one or more embodiments, the bodies 12A and/or 12B and/or 12C are shaped and dimensioned to accomplish one or more of the following: minimize dead spots that may trap aerosol in chamber; minimize impactive losses on the wall of the reservoir during inspiration; minimize settling or sedimentation; minimize recirculation; and combinations thereof. In one or more embodiments, the foregoing is achieved by one or more of chamber shape, air inlet geometry; air inlet placement; air inlet size; aerosol inlet geometry, aerosol inlet placement, aerosol inlet size and air outlet geometry, air outlet placement, and air outlet size. In one or more embodiments, the foregoing is achieved by configuring and dimensioning of the bodies 12A and/or 12B and/or 12C. In one or more embodiments, the foregoing is achieved by the generally bifrustrum shape of the body 12. In one or more embodiments, the foregoing is achieved by positioning the nebulizer 14 at the top of the body 12 to dispense the aerosol plume 21 downwardly, and/or by angling the nebulizer 14 to dispense the aerosol plume 21 non-vertically.

In one or more embodiments, the bodies 12 defining the chamber 22 are shaped to effectuate and/or optimize one or more of the following functional parameters: (i) an ability to empty the chamber 22 of the aerosol plume 21 with a single patient inspiration; (ii) a chamber 22 major dimension, such as height, such that it is sufficient so that the aerosol plume 21 no longer propelled by the nebulizer 14 will not settle through gravity and impact on the lower end of the chamber 22, (such as onto the elbow 30) between a typical patient breathing cycle, for example the plume 21 will not settle for at least about 5 or 4 or 3 or 2 seconds.

The device operates as follows. The reservoir 62 of the nebulizer 14 is filled with a medicament to be aerosolized, and the nebulizer 14 is positioned in the nebulizer port 24 and is operatively connected to the power source and control device 87. The control device 87 may use to simply switch the nebulizer 14 on or off, or it may be used to control timing and modes of nebulization. The patient interface device 16 (such as mouthpiece 102) is coupled to the port 26, and appropriately to the patient. The optional tubing port 28 may be fluidically connected to a port on the control device sets of nebulization ceases when the patient removes the device from his or her mouth. Nebulization is then initiated by the patient/user, or caregiver. As nebulization commences, the nebulized medicament comprising particles 79, forms the aerosol plume 21, which fills the interior of the chamber 22. As the patient inhales via the mouthpiece 102, external air is drawn into plenum 54 through the ports 56. This external air is then drawn into body 12C through port 20 and valve 32, and upwardly into chamber 22 where it mixes with the aerosol plume 21 flowing downwardly. The device 12 thus provides for a countercurrent mixing of nebulized medicament and ambient air. The mixture of aerosolized medicament and ambient air is then drawn up into the body 12A, and out through the mouthpiece 102 solely by the patient's inspiration. As the patient continues to inhale through the mouthpiece 102, the mixture of air and aerosolized is drawn into the patient's lungs. In one of more embodiments, the airflow afforded by the various components results in a beneficial mixing of medicament with air, with concomitant maintenance of an optimal medicament air ratio for the patient. This air:medicament ratio may be adjusted depending on the medicament being dispensed, and upon the patient's characteristics, such as age, physical condition and respiratory characteristics.

In one or more embodiments, a supplemental gas, such as oxygen, helium, or heliox, is introduced into the oxygen accumulation chamber 59 via the port 58. The rate at which oxygen is introduced may vary, depending upon factors such as patient's characteristics, such as age, physical condition and respiratory characteristics. The oxygen, or other gas, in the chamber 59 mixes with ambient air admitted via the port or ports 56, which then mixes with the aerosol plume 21 in the chamber 22 as described.

In one or more embodiments, a mode of operation is thus: during an inhalation phase valve 32 opens permitting ambient air to enter the chamber 22. Upon exhalation, valve 32 closes, which provides sufficient back-pressure within the chamber 22 to impede or prevent air (and unused medicament) exhaled by the patient from flowing into or through the chamber 22, but is instead preferentially expelled through the exhalation exhaust port 104. In one or more embodiments of the invention, the nebulizer 14 operates continuously and during the patient's expiration phase, the aerosol continues to be produced and is stored in chamber 22 for the next inhalation. This mode of operation affords simplicity and efficiency in administration, as patient breathing characteristic do not need to be measured, nor does the controller require extensive circuitry responsive to such measurements. In one or more embodiments, the nebulizer 14 operates continuously, except that the controller 87 includes a shut-off means to shut off the nebulizer 14 if and when the patient interrupts breathing into the interface device 16. The shut off means could, in some embodiments, comprise a simple pressure or flow sensor, and appropriate control circuitry. In one or more embodiments, the nebulizer can be operated intermittently, phasically, or be breath actuated, such that aerosol is inhaled in different patterns as related to a given patient's inspiratory and/or expiratory cycles.

In one or more embodiments, the aerosol generator controller may be configured to shut off the aerosol generator after one or more parameters, qualities or thresholds (as described above) are reached, such as shutting of the aerosol generator after a predetermined amount of nebulization time, and/or after a predetermined amount of liquid is aerosolized.

In one or more embodiments of the device 10, exhaled gas from the patient should exit the system 10 without disturbing the aerosol plume 21 entering the chamber 22. This can be accomplished in at least the following ways: (i) by configuring an expiration port at the patient interface device 16, or between the patient interface device 16 and the chamber 22; (ii) by configuring an inspiratory one way valve at a distal end of the chamber 22 (for example valve 32) with a fixed orifice (resistor) at the patient interface device 16, or between the patient interface device 16 and the chamber 22.

In embodiments employing a one way valve (such as valve 32) and a fixed orifice resistor (such as port 104), some gas will pass through the orifice on both inspiration and expiration. On inspiration a sufficient volume of inhaled gas flows through the chamber 22 to clear the aerosol from the chamber 22. This is accomplished by configuring the one-way valve 32 to have less resistance than that of the fixed orifice 104. For example, with a typical 500 mL tidal volume and a 30 lpm peak inspiratory flow rate, a 350 mL reservoir could be cleared, with sufficient "chase" gas (>75 mL) clearing the anatomical volume of the upper airway, as long as only 50-75 mL enters through the orifice 104. In one or more embodiments, this is achieved by selection of the diameter of the port 104 (or fixed orifice, or other structural resistance to flow) in combination with the resistance of the valve 32, which then balance the inspiratory leakage.

The balance of inhaled gas passing through the chamber 22 and through the orifice 104 can be engineered through the diameter and resistance of both the orifice 104 and those of the one-way valve 32. In one or more embodiments, an orifice 104 diameter may be selected to generate a peak of 5-10 cm $H_2O$ of positive airway pressure on typical passive expiration. This level of pressure is benign as to lung expansion, barotrauma or cardiovascular stress, and has been associated with improved response to aerosols such as bronchodilators, and improved stability (splinting) of airways during exhalation.

In one or more embodiments of the invention, the nebulizer 14 comprises a metered-dose pressurized-canister aerosol generator.

In the above-mentioned configurations, the arrangement of the openings and valves may vary in terms of their position, the Figures being described and cited merely by way of example.

By utilizing an aerosol generator that produces aerosol by the electric powering of a vibratable member that causes an aperture plate to eject liquid at one face thereof, through its apertures, as a mist from the other face thereof, as generally described above (and as described in U.S. Pat. Nos. 5,164, 740; 5,938,117; 5,586,550; 5,758,637, 6,085,740; and 6,235, 177, the complete disclosures of which are, and have been above, incorporated herein by reference), the starting and stopping of aerosol generation may be controlled on the level of accuracy of microseconds or milliseconds, thus providing accurate dosing. The timing of aerosol generation can be done based upon a predetermined timing within a breathing cycle, on timing in conjunction with the length of a prior breath or portions thereof, on other breathing characteristics, on particular medication being administered, or a combination of any of these criteria.

Exemplary Medicaments

Embodiments of the invention contemplate a variety of medicaments that can be aerosolized and delivered to a patient's lungs. These medicaments may comprise antibiotics such as aminoglycosides, .beta.-lactams, glycopeptides and quinolines, among others. The aminoglycosides may comprise amikacin, gentamycin, kanamycin, streptomycin, neomycin, netilmicin, and tobramycin, among other aminoglycosides. Further classes include: glycopeptides such as vancomycin; oxazolidinones, such as linezolid; Beta-lactams such cephalosporins, and cyclosporins such as cyclosporine A and cyclosporine B. Other medicaments may also be used, alternatively or additionally, including anti-infectives, antivirals, anti-oxidants, bronchodilators, corticosteroids, leukotrienes, prostacyclins, protease inhibitors, vaccines, and surfactants, among other medicaments. Table 2 lists exemplary classes of medicaments and some of the aliments they may be used to treat in their aerosolized state, however, the disclosure of Table 2 is exemplary only, and not to be construed as limiting.

TABLE-US-00002 TABLE 2 Classes of Aerosolizable Medicaments Medicament Duration of Class Aliments Treated Dosing Treatment Antibiotics Respiratory infections; 1-2 per day 1-14 days Pneumonia Anti-oxidants RDS, Prevention of 1-4 per day Duration of BPD, ALI, ARDS ventilation Bronchodilators Asthma, COPD, ARDS, 1-4 per day As needed RDS Corticosteroids Asthma, COPD, BPD 1-2 per day Duration of ventilation Leukotrienes or Immu- 1-4 per day 5-14 days related agonists COPD, Treatment/prevention of pneumonia or RSV infection Prostacyclin or PPHN, Secondary Continuous As needed related analogues pulmonary hypertension, Post-cardiac surgery, ARDS Protease AECOPD, ARDS, RDS, 1-2 per day 5-14 days inhibitors BPD Surfactants RDS, Prevention of 1-2 per day As needed BPD, ARDS Anti-RSV, Influenzas, 1-2 per day As needed Infectives/Anti-Respiratory diseases virals AECOPD: acute exacerbation of COPD; ALI: Acute lung injury; ARDS: Acute respiratory distress syndrome; BPD: Bronchopulmonary dysplasia; COPD: chronic obstructive pulmonary disease; PPHN: persistent pulmonary hypertension; RDS: Respiratory distress syndrome (also known as infant respiratory distress syndrome); RSV: Respiratory syncytial virus.

With specific reference to antibiotics, they may be characterized by pharmacodynamic properties that describe killing activity: time-dependence, concentration-dependence, and persistent effects. The rate of killing is determined by either the length of time necessary to kill (time-dependent), or the effect of increasing concentrations (concentration-dependent). Persistent effects include the Post-Antibiotic Effect (PAE). PAE is the persistent suppression of bacterial growth following antibiotic exposure.

Using these parameters, antibiotics may be divided into 3 categories as shown in Table 3 below. This Table is only exemplary, and not intended to limit the methods of administering these antibiotics only to the "Goals of Therapy" listed in Column 3.

TABLE-US-00003 TABLE 3 PK/PD Pattern of Activity Antibiotics Goal of Therapy* Parameter Type I Aminoglycosides Maximize 24 h-AUC/Concentration-Daptomycin concentrations MIC dependent killing Fluoroquinolones Peak/MIC and Ketolides Prolonged persistent effects Type II Carbapenems Maximize T>MIC Time-dependent Cephalosporins duration of killing and Erythromycin exposure Minimal persistent Linezolid effects Penicillins Type III Azithromycin Maximize amount 24 h-AUC/Time-dependent Clindamycin of drug MIC killing and Oxazolidinones Moderate to Tetracyclines prolonged Vancomycin persistent effects.

For Type I antibiotics (AG's, fluoroquinolones, daptomycin and the ketolides), the ideal dosing regimen would maximize concentration, because the higher the concentration, the more extensive and the faster is the degree of killing. Therefore, the 24 h-AUC/MIC ratio, and the Peak/MIC ratio are important predictors of antibiotic efficacy. For aminoglycosides, it is best to have a Peak/MIC ratio of at least 8-10 to prevent resistance. For fluoroquinolones versus gram negative bacteria, the optimal 24 h-AUC/MIC ratio is approximately 12 versus gram positives, and 40 may be optimal in some circumstances.

Type II antibiotics (beta-lactams, clindamycin, erythromcyin, and linezolid) demonstrate the complete opposite properties. The ideal dosing regimen for these antibiotics maximizes the duration of exposure. The T>MIC is the parameter that best correlates with efficacy. For beta-lactams and erythromycin, maximum killing is seen when the time above MIC is at least 70% of the dosing interval.

Type III antibiotics, including vancomycin as well as tetracyclines, azithromycin, and the dalfopristin-quinupristin combination, have mixed properties. They have time-dependent killing and moderate persistent effects. The ideal dosing regimen for these antibiotics maximizes the amount of drug received. Therefore, the 24 h-AUC/MIC ratio is the parameter that correlates with efficacy. For vancomycin, a 24 h-AUC/MIC ratio of at least 125 is necessary (some researchers recommend a ratio of 400 or more for problem bugs).

Embodiments of the invention include methods of administering aerosolized vancomycin to a patient that reflects the antibiotic's Type III classification. The methods include administering vancomycin such that a ratio of an amount of the antibiotic delivered to the patient in a 24-hour period to a minimum inhibitory amount for the same period is about 100 or more (e.g., the ratio is about 125 or more, about 200 or more, about 300 or more, about 400 or more, etc.). The goal of these administration methods is to increase the amount of vancomycin delivered instead of maximizing the peak concentration of the antibiotic in the patient or maximizing the duration of exposure. The methods may also include delivering the aerosolized vancomycin in an intermittent (e.g., phasic) or continuous manner.

Antiinfectives such as antivirals comprise entry-blocking drugs, drugs that interfere with viral synthesis and those that inhibit release of the virus from the host. Thus neuraminidase inhibitors, hemagglutinin inhibitors, and M2 blockers may be delivered in accordance with the present invention. Examples include RNases, zanamivir, oseltamivir, zidovudine, and rimantadine, to name a few.

Embodiments of the invention contemplate administration of a variety of vaccines, such as those directed to Mumps, Rubella and combined MMR; Flu (Seasonal, SARS, Avian); Hantivirus; Pneumococcol; Bacterial/eukaryotic; Malaria; Smallpox; Anthrax; Meningococcal; Tuberculosis; and *Francisella tularenis*.

Vaccines are generally reconstituted dry powders, and as such storage instable, heat labile and are thus short-lived, dictating reconstitution immediately before use, and disposal of any remaining portion immediately thereafter.

In view of the above, the aerosolized liquid may comprise an active agent. The active agent described herein comprises an agent, drug, compound, composition of matter, or mixture thereof, which provides some pharmacologic, often beneficial, effect. As used herein, the term further includes any physiologically or pharmacologically active substance that produces a localized or systemic effect in a patient. An active agent for described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, antidepressants, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, angiotensin II receptor blockers, epithelium sodium channel blockers, bronchodilators, anticholinergics, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally, systemically, or both.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents or medicaments suitable for use in this invention include but are not limited to one or more of amiloride, calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-2 fusion protein, interleukin-1 receptor antagonist, interleukin-3, interleukin-4, interleukin-6, interleukin-11, luteinizing hormone releasing hormone (LHRH), insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulin-like growth factor binding protein (e.g., IGFBP3), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFTR) gene, deoxyreibonuclease (DNase), bactericidal/permeability increasing protein (BPI), anti-CMV antibody, 13-cis retinoic acid, 9-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetonide, budesonide acetonide, fluticasone, ipratropium bromide, flunisolide, cromolyn sodium, ergotamine tartrate; rilapladib, darapladib, remogliflozin etabonate, otelixizumab, carvedilol, fondaparnux, metformin, rosiglitazone, farglitazar, sitamaquine, tafenoquine, belimumab, pazopanib, ronacaleret, solabegron, dutasteride, mepolizumab, ofatumumab, orvepitant, casopitant, firategrast, lamotrigine, ropinirole, iboctadekin, rituximab, totrombopag, lapatinib, elesclomol, topotecan, darotropium, zafirlukast, anastrozole, candesartan cilexetil, bambuterol, terbutaline, mepivacaine, bicalutamide, prilocaine, rosuvastatin, propofol, fulvestrant, isosorbide-5-mononitrate, isosorbide dinitrate, propanolol, gefitinib, enalapril, felodipine, metoprolol, omeprazole, bupivacaine, primidone, ropivacaine, esomeprazole, atenolol, nifedipine, tamoxifen, formoterol, ramipril, quetiapine, chlorthalidone, raltitrexed, viloxazine, lisinopril, hydrochlorothiazide, goserelin, zolmitriptan, saxagliptin, dapagliflozin, motavizumab, ibuprofen, ethinyl estradiol, levonorgestrel, loratadine, amiodarone, brompheniramine, dextromethorphan, phenylephrine, phenylpropanolamine, venlafaxine, etanercept, norgestrel, minocycline, gemtuzumab ozogamicin, oprelvekin, pantoprazole, promethazine, medroxyprogesterone, epinephrine, desvenlafaxine, sirolimus, temsirolimus, ethionamide, tigecycline, tazobactam, bazedoxifene, priniberel, bifeprunox, bapineuzumab, lecozotan, vabicaserin, rotigaptide, stamulumab, methylnaltrexone, bosutinib, alteplase, tenecteplase, meloxicam, tamsulosin, tiotropium, salbutamol, fenoterol, nevirapine, tipranavir, duloxetine, pramipexole, dipyridamole, naproxen, bevacizumab, sulfamethoxazole trimethoprim, benzafibrate, ibandronate, mycophenolate mofetil, enfuvirtide, trastuzumab, saquinavir, granisetron, mefloquine, levodopa benserazide, epoetin beta, filgrastim, dornase alfa, isotretinoin, oseltamivir, erlotinib, ketorolac, torasemide, valganciclovir, diazepam, tretinoin, nelfinavir, capecitabine, orlestat, daclizumab, tocilizumab, ocrelizumab, aleglitazar, pertuzumab, nicaraven, omalizumab, risedronate, fexofenadine, zolpidem, dolasetron, leflunomide, irbesartan, clindamycin, fluorouracil, leuprolide, rasburicase, oxaliplatin, hyaluronate, telithromycin, glargine, enoxaparin, ciclopirox, clopidogrel, riluzole, poly-L-lactic acid, docetaxel, alfuzosin, glimepiride, chloroquine, mepenzolate, clomiphene, desmopressin, meperidine, prednicarbate, glyburide, ergocalciferol, methanamine, hydrocortisone, betaxolol, furosemide, indapamide, ambenonium, nilutamide, metronidazole, desipramine, hydroxychloroquine, rifapentine, milrinone, diflorasone, rifampin, tiludronate, pentazocine, pentoxyifylline, hyaluronic acid, benzalkonium, tissue-plasminogen activator, CMV immune globulin, glucocerebrocidase, trimetrexate, porfimer, sterile thiotepa, amifostine, doxorubicin, 3TC, daunorubicin, cidofovir, carmustine, mitoxantrone, HIV protease inhibitor, dopamine DA1 agonist, carbamazepine, sermorelin, peptide GP Ifb/IIIa antagonist, palivizumab, thalidomide, infliximab, fomivirsen, doxycycline, sevelamer, modafinil, antithymocyte globulin, hepatitis B immune globulin, amprenavir, cytarbine, zanamivir, bexarotene, somatropin, zonisamide, verteporfin, colesevelam, direct thrombin inhibitor, thrombin, antihemophilic factor, methylphenidate, arsenic trioxide, choriogonadotropin alpha, hyaluronan, epivir, retrovir, ziagen, bivalirudin, intron, alemtuzumab, triptorelin, nesiritide, osteogenic protein, tenofovir disoproxil, bosentan, endothelin receptor antagonist, dexmethylphenidate, 5HT 1B/1D agonist, Y2B8, secretin, treprostinil, sodium oxybate, prasterone, adefovir dipivoxil, mitomycin, adalimumab, alefacept, agalsidase beta, laronidase, gemifloxacin, tositumomab, iodine, nucleoside reverse transcriptase inhibitor, palonosetron, gallium nitrate, efalizumab, risperidone, fosamprenavir, abarelix, tadalafil, cetuximab, cinacalcet, trospium, rifaximin, azacitidine, emtricitabine, erlotinib, natalizumab, eszopiclone, palifermin, aptaninb, clofarabine, iloprost, pramlintide, exenatide, galaplase, hydralazine, sorafenib, lenalidomide, ranolazine, naltrexone, alglucosidase alfa, decitabine, ranibizumab, efavirenz, emtracitabine, idursulfase, oravescent fentanyl, panitumumab, telbivudine, aliskiren, eculizumab, ambrisentan, armodafinil, lanreotide, sapropterin, rimantidine, valsartin, losartin, atorvastatin, and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, RNAi, aptamers, siRNA, vectors, associated viral particles, plasmid DNA or RNA or other nucleic acid constructions of a type suitable for transfection or transformation of cells, i.e., suitable for gene therapy including antisense, and stem cells. Further, an active agent may comprise live attenuated or killed viruses suitable for use as vaccines, such as cytomegalovirus, rabies, HIV, *S. pneumoniae*, Dengue fever, Epstein-Barr, West Nile, hepatitis, malaria, tuberculosis, Vericella Zoster, influenza, herpes, diphtheria, tetanus, pertussis, acellular pertussis, human papilloma, BCG, Hib-MenCY-TT, and MenACWY-TT. The active agent may also comprise antibodies, such as monoclonal antibody or monoclonal antibody fragment, such as anti-CD3 mAb, digoxin-binding ovine antibody fragment, anti-RSV Ab, anti-TAC mAb, or anti-platelet mAb. Other useful drugs include those listed within the Physician's Desk Reference (most recent edition).

EXPERIMENTAL

The results demonstrate that the device according to the invention makes it possible to increase the fraction of aerosol that can be inhaled by the patient. The device provides an increase in the performance of aerosol generators to 50% or more, and as high as 95%, in terms of the inhalable aerosol mass. The device does not influence the duration of nebulization, thus the device can be used to increase the aerosol flow rate administered to the patient.

Example 1

Figure 9:
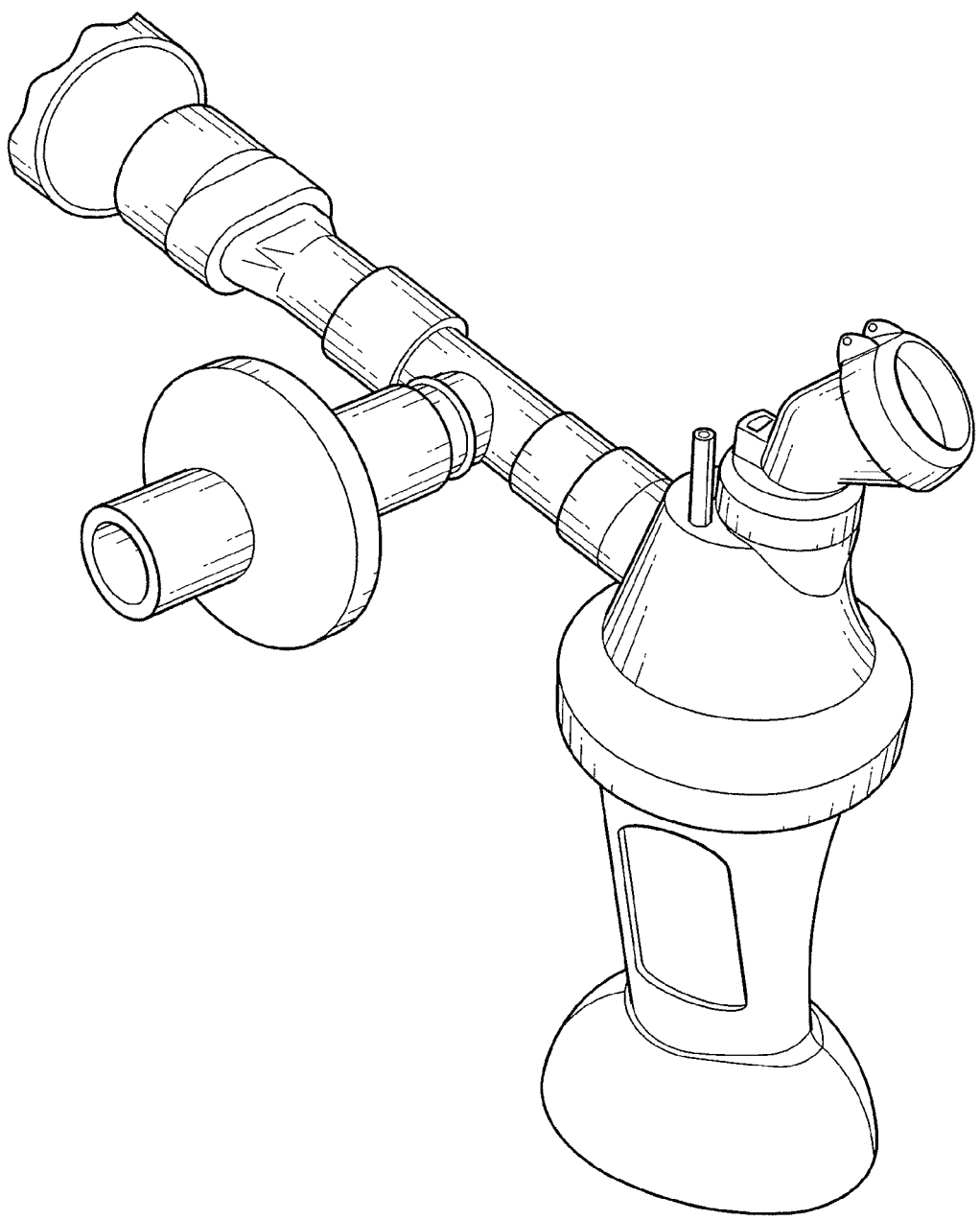
FIG. 9 is a perspective view of an experimental set up.

In this Example an in-vitro delivered dose and particle size distribution (PSD) of the device of FIG. 1 was measured, using a dose of 400 mg of amikacin (125 mg/ml; 3.2 ml). Thus, the in-vitro percentage inhaled mass of amikacin sulfate at the mouthpiece under simulated patient breathing was quantified. Under the following conditions: Tidal Volume (TV) was 500 mL; Respiratory rate (RR) was 15 and an inspiratory to expiratory ratio was 2:3. Three devices were tested. Also, an in-vitro particle size distribution (PSD) at the was determined. Mass balance was determined at the end of the first inhaled mass test run. Breathing parameters of the ventilator were verified pre- and post-inhaled mass test runs. The experimental set up is depicted in FIG. 9.
Results and Discussion.

Figure 10:
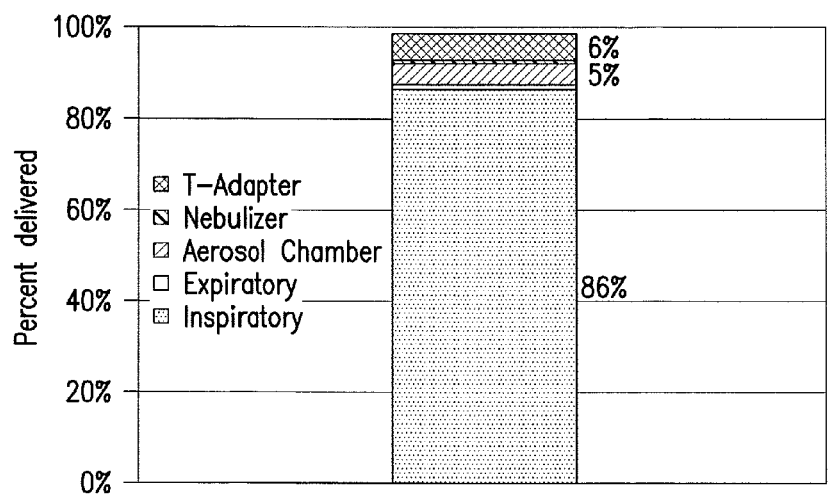
FIG. 10 is a stacked bar chart showing inhaled mass balance achieved with devices and methods of the present invention.

FIG. 10 is a stacked graph showing 98% mass balance after one run. It can be seen that 86% was delivered as measured by the washing and elution method described herein, which 5% and 6% remained in the chamber and t-piece, respectively.

Figure 11:
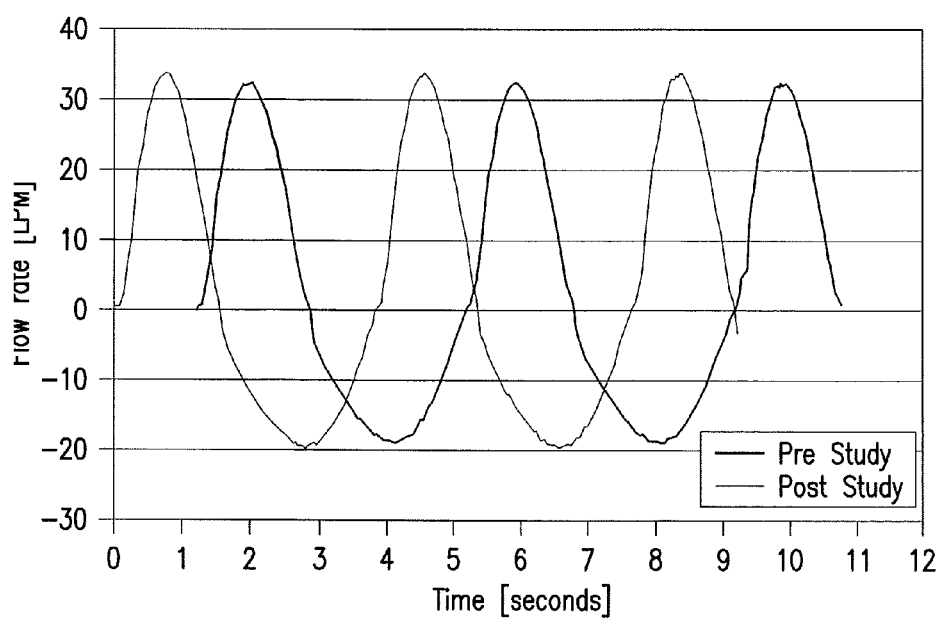
FIG. 11 is a graph showing a patient's breathing profiles, pre and post testing.

FIG. 11 is a graph showing breathing profiles to be comparable pre and post testing. This means that the use of the device, and the associated methods, of the present invention, beneficially do not influence or change the patient's breathing pattern or characteristics.

Figure 12:
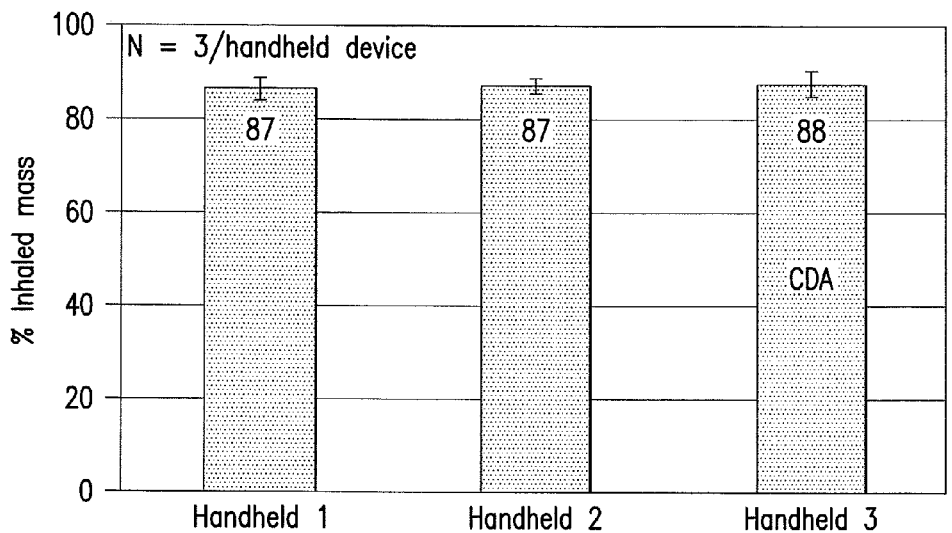
FIG. 12 is a bar chart showing comparable inhaled mass for three devices of the present invention.

FIG. 12 is a bar chart for three devices in accordance with Example 1, showing percentage of inhaled mass delivered by the device. Overall mean inhaled mass of 87% was achieved at the mouthpiece for the simulated breathing pattern, showing good reproducibility.

Figure 13:
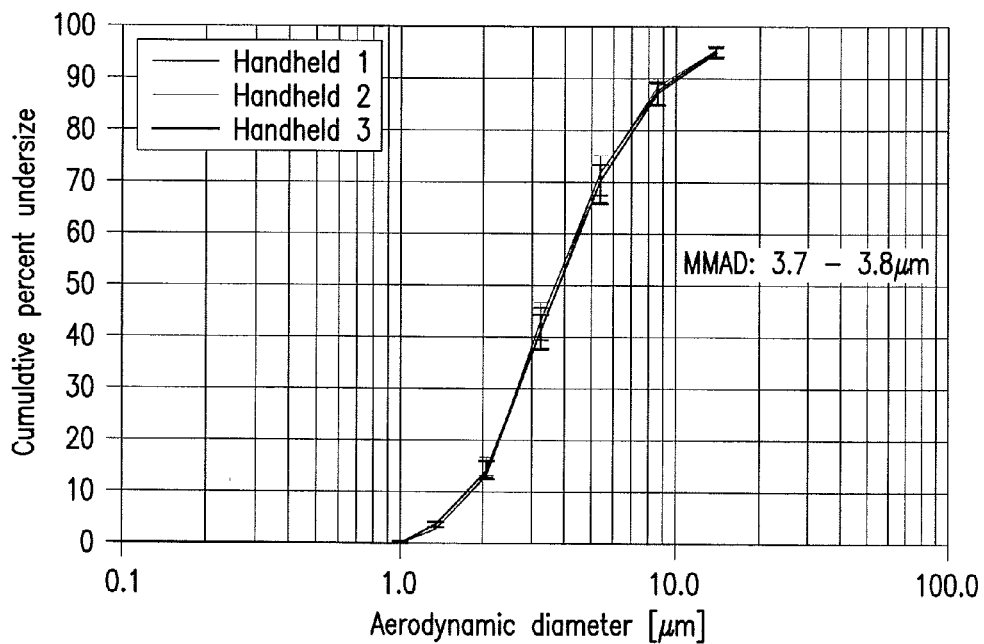
FIG. 13 is a graph showing comparable mass median aerodynamic diameter (MMAD) of aerosolized particles for three devices of the present invention.

FIG. 13 is a graph showing Particle Size Distribution (PSD) at the mouthpiece. A Comparable PSD across the three hand-held devices was demonstrated, showing good reproducibility.

A Mass Median Aerodynamic Diameter (MMAD) of the aerosolized particles of 3.7-3.8 μm was measured at the mouthpiece for the three hand-held devices. A Fine Particle fraction of less than 5 microns (FPF$_{<5.0}$ μm) was about 66%, and a Fine Particle Dose of less than 5 microns (FPD$_{<5.0}$ μm) was about 240 mg.

Example 2

Figure 14:
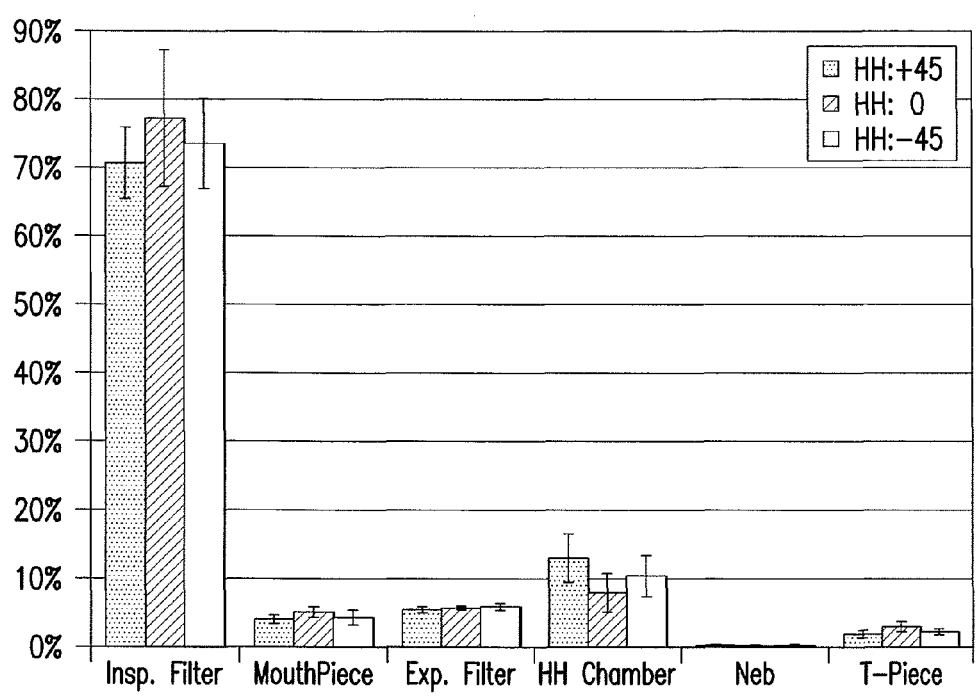
FIG. 14 is a bar chart showing mass balance for three different orientations of the aerosolization device of the present invention.

In this Example, inhaled mass, and nebulization times, for a device of the present invention, as illustrated in FIG. 1, was measured for three different orientations with respect to the central axis AA: −45 degrees, 0 degrees and +45 degrees, i.e. tipped over toward the simulated patient, upright, and tipped away from the simulated patient, respectively. Since the aerosolized outlet port is inclined at an upward angle (see FIG. 1) of about 20, this resulted in the mouthpiece being angled at about −25°, 20° and 65° respectively. Test conditions were as described in Example 1. Three devices, comprising Aerogen nebulizers, as depicted in FIGS. 1 and 6 were used for the test.
Results and Discussion Nebulization times as a function of orientation (average of three devices) were found to be: −45=10 minutes; 0=12 minutes and +45=11 minutes. The nebulizers were found to have an estimated flow rate of about 0.36 mL/min (nebulizer #1); 0.25 mL/min (nebulizer #2); 0.36 mL/min (nebulizer #1). FIG. 14 is a bar graph showing mass balance for the three orientations. As can be seen, about 78% of the aerosol mass was deposited on the inspiratory filter (as surrogate for the patient's pulmonary system) for the device in the 0 inclination, while the two 45 orientations resulted in about 71% and 74% deposition. Total recovered mass averaged about 99% for the 0 inclination device, while the two 45 orientations resulted in about 95% and 97%. Deposition on the mouthpiece, expiratory filter aerosolization chamber nebulizer and T-piece are presented in the graph for each orientation.

Figure 15B:
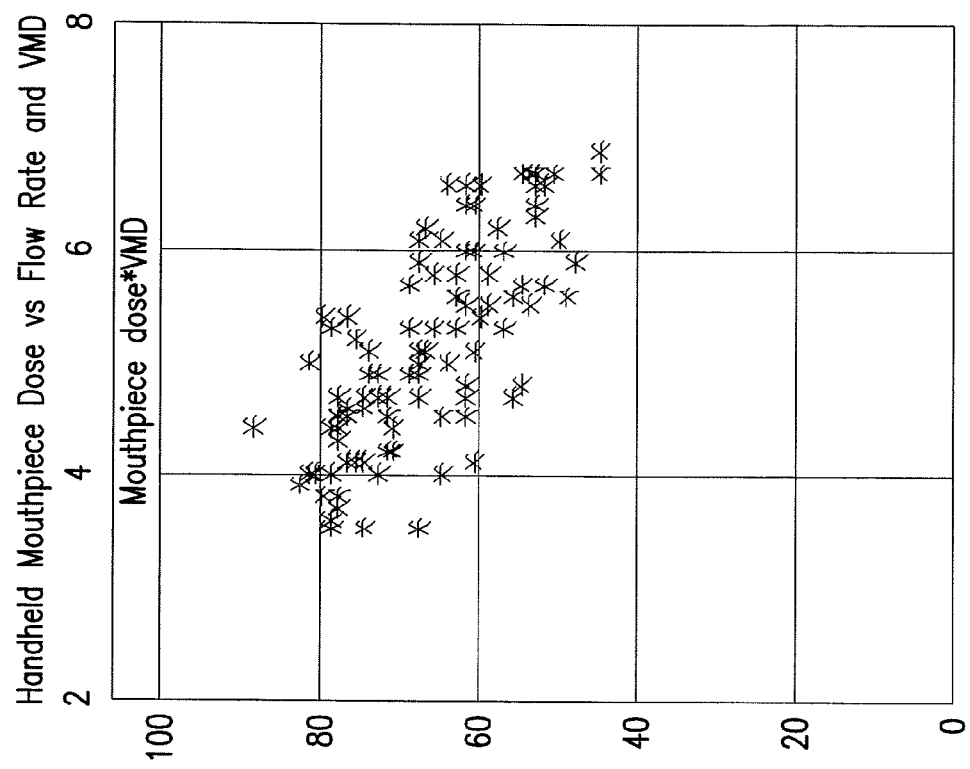
FIGS. 15A and 15B are a plots of delivered dose (mouthpiece) verses flow rate (FIG. 15A) and volume mean diameter particle size (FIG. 15B) for an amikacin formulation aerosolized with a device of the present invention.
Figure 15A:
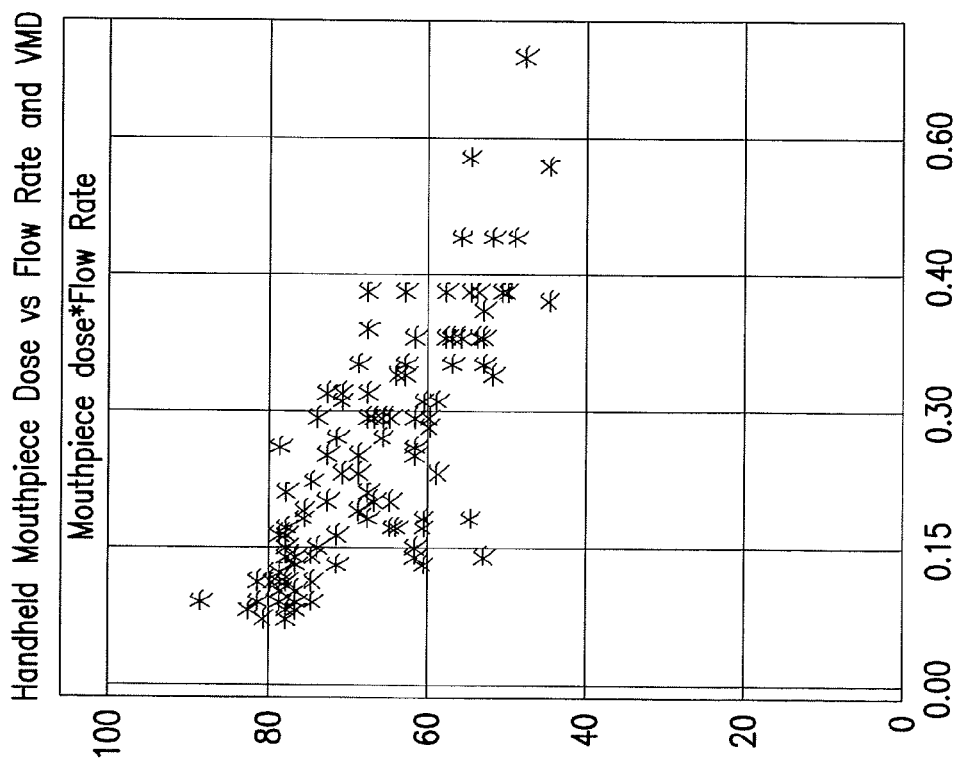
Figure 16:
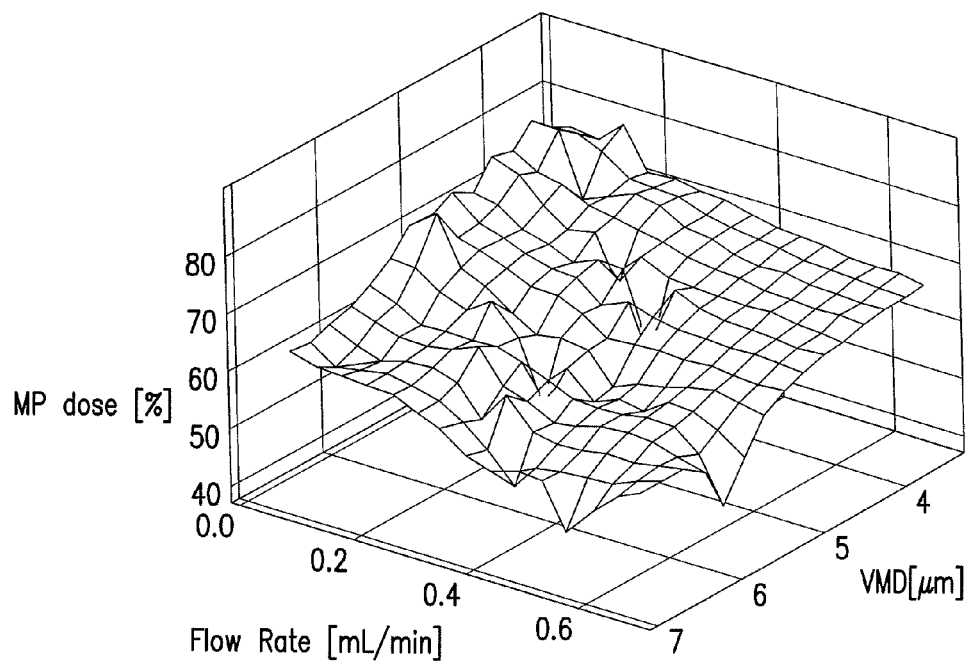
FIG. 16 is a contour plot of the data presented in FIG. 15, showing delivered dose (mouthpiece) versus both flow rate and particle size for an amikacin formulation aerosolized with a device of the present invention.

FIGS. 15A and 15B are a plots of delivered dose (mouthpiece) verses flow rate (FIG. 15A) and volume mean diameter particle size (FIG. 15B) for an amikacin formulation aerosolized with a device of the present invention, and FIG. 16 is a contour plot of the data presented in FIG. 15. Percent delivered was measured at the mouthpiece as percent of nominal amikacin solution (as 3.2 mL of solution). Flow rate is shown in mL per minute, and particle size in microns. The aerosolization device was substantially as depicted in FIG. 1.

Although the present invention has been described in detail with regard to certain preferred versions thereof, other versions are possible, and alterations, permutations and equivalents of the version shown will become apparent to those skilled in the art upon a reading of the specification. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. A method of administering a medicament to a patient, the method comprising
    inhaling a dose of an aerosolized medicament by the patient, wherein said dose of the aerosolized medicament is provided by
    an aerosol device comprising:
    an aerosol accumulation chamber having a central vertical axis, an upper end and a lower end, the upper end comprising a nebulizer port and a patient interface port, the lower end comprising an air inlet port, wherein the air inlet port is oriented to be non-aligned with said central vertical axis, said air inlet port further comprising a valve;
    an outer shell, substantially surrounding the at least said lower end of the aerosol accumulation chamber, the outer shell having one or more air inlet passages about a periphery thereof wherein said one or more air inlet passages is above said air inlet port, said patient interface port fluidically coupled to a patient interface device, and an aerosolized exhaust port intermediate to said patient interface device and to said patient interface port;
    a vibrating mesh nebulizer that is fluidically coupled to said nebulizer port; and a liquid medicament for aerosolization to generate said dose of the aerosolized medicament via the vibrating mesh nebulizer.

2. The method of claim 1, wherein said dose is inhaled within one to four minutes.

3. The method of claim 2, wherein said dose is inhaled within one minute.

4. The method of claim 1, wherein said liquid medicament comprises an aqueous solution.

5. The method of claim 4, wherein said liquid medicament is preservative-free.

6. The method of claim 1, wherein said liquid medicament comprises amikacin sulfate.

7. The method of claim 1, wherein the liquid medicament comprises amikacin.

8. The method of claim 1, wherein said liquid medicament comprises vancomycin.

* * * * *